United States Patent
Natala et al.

(10) Patent No.: US 10,189,824 B2
(45) Date of Patent: Jan. 29, 2019

(54) PYRIMIDINE-DIAMINE DUAL HSP90/TRAP1 INHIBITORS

(71) Applicant: CalAsia Pharmaceuticals, Inc., San Diego, CA (US)

(72) Inventors: Srinivasa Reddy Natala, San Diego, CA (US); Sridhar G. Prasad, San Diego, CA (US)

(73) Assignee: Calasia Pharmaceuticals, Inc., San Diego, CA (US)

( * ) Notice: Subject to any disclaimer, the term of this patent is extended or adjusted under 35 U.S.C. 154(b) by 46 days.

(21) Appl. No.: 15/509,608

(22) PCT Filed: Sep. 11, 2015

(86) PCT No.: PCT/US2015/049694
§ 371 (c)(1),
(2) Date: Mar. 8, 2017

(87) PCT Pub. No.: WO2016/040807
PCT Pub. Date: Mar. 17, 2016

(65) Prior Publication Data
US 2017/0247358 A1 Aug. 31, 2017

Related U.S. Application Data

(60) Provisional application No. 62/049,095, filed on Sep. 11, 2014.

(51) Int. Cl.
*A61K 31/506* (2006.01)
*C07D 401/14* (2006.01)
*C07D 405/14* (2006.01)
*C07D 401/12* (2006.01)

(52) U.S. Cl.
CPC .......... *C07D 405/14* (2013.01); *A61K 31/506* (2013.01); *C07D 401/12* (2013.01); *C07D 401/14* (2013.01)

(58) Field of Classification Search
CPC .......................... A61K 31/506; C07D 401/14
USPC ........ 514/272, 275; 544/295, 296, 320, 321, 544/324
See application file for complete search history.

(56) References Cited

FOREIGN PATENT DOCUMENTS

WO 2013/172872 A1 11/2013

OTHER PUBLICATIONS

N. Gaspar, et al., "Mechanistic evaluation of the novel HSP90 inhibitor NVP-AUY922 in adult and pediatric glioblastoma", Mol. Cancer. Ther., May 2010, vol. 9, No. 5, pp. 1219-1233.

J. R. Porter, et al., "Discovery and development of Hsp90 inhibitors: a promising pathway for cancer therapy", Current Opinion in Chemical Biology, (2010), vol. 14, pp. 412-420.
J. T. Ernst, et al., "Identification of Novel HSP90α/β Isoform Selective Inhibitors Using Structure-Based Drug Design. Demonstration of Potential Utility in Treating CNS Disorders such as Huntington's Disease", Journal of Medicinal Chemistry, (2014), vol. 57, pp. 3382-3400.
E. Constantino, et al., "TRAP1, a novel mitochondrial chaperone responsible for multi-drug resistance and protection from apoptotis in human colorectal carcinoma cells", Cancer Letters, (2009), vol. 279, pp. 39-46.
F. Maddalena, et al., "Resistance to paclitxel in breast carcinoma cells requires a quality control of mitochondrial antiapoptotic proteins by TRAP1", Molecular Oncology, (2013), vol. 7, pp. 895-906.
Y. C. Chae, et al., "Control of Tumor Bioenergetics and Survival Stress Signaling by Mitochondrial HSP9Os", Cancer Cell, Sep. 11, 2012, vol. 22, No. 3, pp. 331-344.
D. S. Matassa, et al., "Translational control in the stress adaptive response of cancer cells: a novel role for the heat shock protein TRAP1", Cell Death and Disease, (2013), vol. 4, pp. 1-10.
S. J. Felts, et al., "The hsp90-related Protein TRAP1 is a Mitochondrial Protein with Distinct Functional Properties", The Journal of Biological Chemistry, Feb. 4, 2000, vol. 275, No. 5, pp. 3305-3312.
M. D. Siegelin, et al., "Global Targeting of Subcellular Hsp90 Networks for Therapy of Gliobastoma", Mol. Cancer. Ther., Jun. 2010, vol. 9, No. 6, pp. 1638-1646.
M. McLaughlin, et al., "The endoplasmic reticulum protein folding factory and its chaperones: new targets for drug discovery?", British Journal of Pharmacology, (2011), vol. 162, pp. 328-345.
B. H. Kang, et al., "Regulation of Tumor Cell Mitochondrial Homeostasis by an Organelle-Specific Hsp90 Chaperone Network", Cell, Oct. 19, 2007, vol. 131, pp. 257-270.
S. Okayama, et al., "p53 Protein Regulates Hsp90 ATPase Activity and Thereby Wnt Signaling by Modulating Aha1 Expression", The Journal of Biological Chemistry, Mar. 7, 2014, vol. 289, No. 10, pp. 6513-6525.
D. C. Alteri, et al., "TRAP-1, The Mitochondrial Hsp90", Biochim Biophys Acta., Mar. 2012, vol. 1823, No. 3, pp. 767-773.

(Continued)

*Primary Examiner* — Brenda L Coleman
(74) *Attorney, Agent, or Firm* — Posternak Blankstein & Lund LLP

(57) ABSTRACT

Provided are novel compounds of Formula (I): pharmaceutically acceptable salts thereof, and pharmaceutical composition thereof, which are useful as dual Hsp90/TRAP1 inhibitors. Also provided are pharmaceutical compositions comprising the novel compounds of Formula (I) and their use in treating one or more cancers.

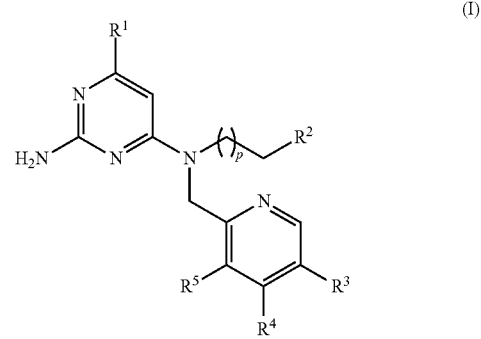

27 Claims, 12 Drawing Sheets

(56) References Cited

OTHER PUBLICATIONS

H. Zhu, et al., "The novel Hsp90 inhibitor NXD30001 induces tumor regression in a genetically engineered mouse model of glioblastoma multiforme", Mol. Cancer Ther., Sep. 2010, vol. 9, No. 9, pp. 2618-2626.

C. M. Sauvageot, et al., "Efficacy of the HSP90 inhibitor 17-AAG in human glioma cell lines and tumorigenic glioma stem cells", Neuro-Oncology, Apr. 2009, pp. 109-121.

R. Bao, et al., "CUDC-305, a Novel Synthetic HSP90 Inhibitor with Unique Pharmacologic Properties for Cancer Therapy", Clin Cancer Res, Jun. 15, 2009, vol. 15, No. 12, pp. 4046-4057.

K. Sidera, et al., "HSP90 Inhibitors: Current Development and Potential in Cancer Therapy", Recent Patents on Anti-Cancer Drug Discovery, (2014), vol. 9, No. 1, pp. 1-20.

W. Xu, et al., "Targeting the Molecular Chaperone Heat Shock Protein 90 Provides a Multifaceted Effect on Diverse Cell Signaling Pathways of Cancer Cells", Clin Cancer Res, Mar. 15, 2007, vol. 13, No. 6, pp. 1625-1629.

J. Munson, et al., "Identifying new small molecule anti-invasive compounds for glioma treatment", Cell Cycle, Jul. 15, 2013, vol. 12, No. 14, pp. 2200-2209.

PYRIMIDINE-DIAMINE DUAL HSP90/TRAP1 INHIBITORS

CROSS REFERENCE TO RELATED APPLICATIONS

The present application claims benefit of U.S. Provisional Application No. 62/049,095 filed on Sep. 11, 2014, the entire contents of which are incorporated herein by reference.

STATEMENT REGARDING FEDERALLY SPONSORED RESEARCH OR DEVELOPMENT

This invention was made with government support under 1R43GM090383 awarded by the National Institutes of Health. The government has certain rights in the invention.

TECHNICAL FIELD

The present disclosure is directed to novel Hsp90/TRAP1 dual inhibitors, processes for their preparation, pharmaceutical compositions containing these inhibitors, and their use in the treatment of cancers.

BACKGROUND

Glioblastoma multiforme (GBM) is the most malignant and invasive human brain tumor and has a 5-year survival rate that remains at less than 5%, despite the use of intensive treatment modalities. The prognosis has remained dismal in spite of aggressive multimodal therapy through implementation of a newer generation of targeted molecular therapies alone or in combination (Munson J, Bonner M, Fried L, Hofmekler J, Arbiser J et al. (2013) Identifying new small molecule anti-invasive compounds for glioma treatment. Cell Cycle 12:2200-9). The development of new treatments is critical in order to improve the outcomes of patients with GBM. In contrast to chemotherapeutically targeting a single protein or signaling pathway in cancer cells, the concept of targeting a master regulator in cancer cells, such as heat shock protein 90 (Hsp90) has gained appeal and may hold promise for highly heterogeneous and invasive cancers like GBM that are refractory to current treatments (Munson J, Bonner M, Fried L, Hofmekler J, Arbiser J et al. (2013) Identifying new small molecule anti-invasive compounds for glioma treatment. Cell Cycle 12:2200-9; and Xu W, Neckers L (2007) Targeting the molecular chaperone heat shock protein 90 provides a multifaceted effect on diverse cell signaling pathways of cancer cells. Clin Cancer Res. 13:1625-9). Newer generations of small molecule Hsp90 inhibitors (Hsp90i) that target the ATP binding pocket are showing promising efficacy against a broad range of cancers, along with improved safety profiles. However, the outcomes of Hsp90i clinical trials, while promising, have been mixed at best, indicating the need for more efficacious Hsp90i (McDonald E, Workman P, Jones K. (2006) Inhibitors of the HSP90 molecular chaperone: attacking the master regulator in cancer. Curr Top Med Chem. 6:1091-107; Sidera K, Patsavoudi E (2014) HSP90 inhibitors: current development and potential in cancer therapy. Recent Pat Anticancer Drug Discov 9:1-20; and Travers J, Sharp S, Workman P (2012) HSP90 inhibition: two-pronged exploitation of cancer dependencies. Drug Discov Today (5-6):242-52). There are at least 13 Hsp90 inhibitor drug candidates that are currently undergoing clinical trials for multiple indications as single agents or combination therapy (Sidera K, Patsavoudi E (2014) HSP90 inhibitors: current development and potential in cancer therapy. Recent Pat Anticancer Drug Discov 9:1-20). These drugs represent a diverse array of chemical matter stemming from natural product scaffolds to synthetic structure-based design (Sidera K, Patsavoudi E (2014) HSP90 inhibitors: current development and potential in cancer therapy. Recent Pat Anticancer Drug Discov 9:1-20; and Porter J R, Fritz C C, Depew K M (2010) Discovery and development of Hsp90 inhibitors: a promising pathway for cancer therapy. Curr Opin Chem Biol 14:412-20). Significantly, of the vast number of small molecule Hsp90 inhibitors described, only a small number are known to cross the blood brain barrier, which is an absolute drug requirement for cancers of the CNS, such as GBM (Bao R1, Lai C J, Qu H, Wang D, Yin L, et al (2009) CUDC-305, a novel synthetic HSP90 inhibitor with unique pharmacologic properties for cancer therapy. Clin Cancer Res. 15:4046-57; Ernst J T, Neubert T, Liu M, Sperry S, Zuccola H, et al (2014) Identification of novel HSP90α/β isoform selective inhibitors using structure-based drug design. Demonstration of potential utility in treating CNS disorders such as Huntington's disease. J Med Chem 57:3382-400; Sauvageot C M, Weatherbee J L, Kesari S, Winters S E, Barnes J, et al. (2009). Efficacy of the HSP90 inhibitor 17-AAG in human glioma cell lines and tumorigenic glioma stem cells. Neuro Oncol. 11:109-121; and Zhu H, Woolfenden S, Bronson R T, Jaffer Z M, Barluenga S, et al. (2010) The novel Hsp90 inhibitor NXD30001 induces tumor regression in a genetically engineered mouse model of glioblastoma multiforme. Mol Cancer Ther. 9:2618-2626).

Hsp90 may be considered a master regulator in cancer cells by virtue of its role as a chaperone protein whose association is required for the stability and function of multiple mutated, chimeric and over-expressed signaling proteins that promote the growth and/or survival of cancer cells. The promise of inhibition of such a master regulator for cancer therapy is the potential to cause combinatorial inhibition of multiple oncogenic signaling pathways simultaneously. With the recent discovery of feedback loops that effectively negate the efficacy of selectively targeted anti-cancer agents, there is renewed interest in such a multi-pronged approach (Altieri D C, Stein G S, Lian J B, Languino L R (2012) TRAP-1, the mitochondrial Hsp90. Biochim Biophys Acta. 1823:767-773; and Siegelin M D (2013) Inhibition of the mitochondrial Hsp90 chaperone network: a novel, efficient treatment strategy for cancer? Cancer Lett 333:133-46).

Hsp90 and the two compartmentalized homologues of Hsp90 that are found in cells, i.e., endoplasmic reticular grp94 and mitochondrial TRAP1, show increased levels and/or increased ATPase activity in many cancers including GBM in response to cellular stress (Okayama S, Kopelovich L, Balmus G, Weiss R S, Herbert B S, et al (2014) p53 protein regulates Hsp90 ATPase activity and thereby Wnt signaling by modulating Aha1 expression. J Biol Chem 289:6513-25; Burrows F, Zhang H, Kamal A (2004) Hsp90 activation and cell cycle regulation. Cell Cycle 3:1530-6; Ferrarini M, Heltai S, Zocchi M R, Rugarli C. (1992) Unusual expression and localization of heat-shock proteins in human tumor cells. Int J Cancer. 51:613-9; Costantino E, Maddalena F, Calise S, Piscazzi A, Tirino V, et al (2009) TRAP1, a novel mitochondrial chaperone responsible for multidrug resistance and protection from apoptosis in human colorectal carcinoma cells. Cancer let 279:39-46; Kang B H, Plescia J, Dohi T, Rosa J, Doxsey S J, et al (2007) Regulation of tumor cell mitochondrial homeostasis by an organelle-specific Hsp90 chaperone network. Cell 131:257-70;

McLaughlin M, Vandenbroeck K (2011) The endoplasmic reticulum protein folding factory and its chaperones: new targets for drug discovery? Br J Pharmacol 162:328-45; and Siegelin M D, Plescia J, Raskett C M, Gilbert C A, Ross A H, et al (2010) Global targeting of subcellular hsp90 networks for therapy of glioblastoma. Mol Cancer Ther 9:1638-1646. Given the significant homology within the ATP binding pockets of these Hsp90 homologues, new generations of Hsp90 inhibitors with broadened activity to include one or both of these homologues could improve efficacy for this inhibitor class (Felts S J, Owen B A, Nguyen P, Trepel J, Donner D B, et al (2000) The hsp90-related protein TRAP1 is a mitochondrial protein with distinct functional properties. J Biol Chem 275:3305-12). Inhibitors that target one or both mitochondrial Hsps (TRAP1 and mitochondrial Hsp90) are particularly attractive based on the finding that mitochondrial Hsps exhibit antiapoptotic and antioxidant proprieties in cancer cells (Matassa D S1, Amoroso M R, Agliarulo I, Maddalena F, Sisinni L, et al (2013) Translational control in the stress adaptive response of cancer cells: a novel role for the heat shock protein TRAP1. Cell Death Dis 4:e851:1-10). TRAP1 promotes tumor growth by virtue of its role in a number of protective processes that include protection against mitochondrial apoptosis and drug resistance (Chae Y C, Caino M C, Lisanti S, Ghosh J C, Dohi T, et al (2012) Control of tumor bioenergetics and survival stress signaling by mitochondrial HSP90s. Cancer Cell 22:331-344; Maddalena F1, Sisinni L, Lettini G, Condelli V, Matassa D S, et al (2013) Resistance to paclitxel in breast carcinoma cells requires a quality control of mitochondrial antiapoptotic proteins by TRAP1. Mol Oncol 7:895-906; and Wang R, Shao F, Liu Z, Zhang J, Wang S, et al (2013) The Hsp90 inhibitor SNX-2112, induces apoptosis in multidrug resistant K562/ADR cells through suppression of Akt/NF-jB and disruption of mitochondria-dependent pathways. Chemico-Biological Interactions 205:1-10). Inhibitors against cytosolic Hsp90 and mitochondrial Hsps have been shown to be effective against GBM, both in vitro and in vivo (Gaspar N, Sharp S Y, Eccles S A, Gowan S, Popov S, et al. (2010) Mechanistic evaluation of the novel HSP90 inhibitor NVP-AUY922 in adult and pediatric glioblastoma. Mol Cancer Ther. 9:1219-1233). In view of these findings, dual Hsp90/TRAP1 inhibitors will be of significant therapeutic benefit, particular in the treatment of GBM and other cancers.

SUMMARY

It has now been found that the compounds described herein, and pharmaceutically acceptable compositions thereof, are effective dual Hsp90/TRAP1 inhibitors. Such compounds include those of Formula (I):

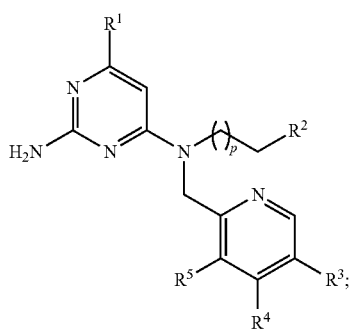

(I)

or a pharmaceutically acceptable salt thereof, wherein $R^1$, $R^2$, $R^3$, $R^4$, and $R^5$ are as described and defined herein.

The provided compounds, and pharmaceutically acceptable compositions thereof, are dual Hsp90/TRAP1 inhibitors and are useful for treating a variety of cancers. Such cancers include those described herein.

The provided compounds can be used alone (i.e., as a monotherapy) or in combination with one or more other therapeutic agent effective for treating any of the indications described herein.

Figure 7:
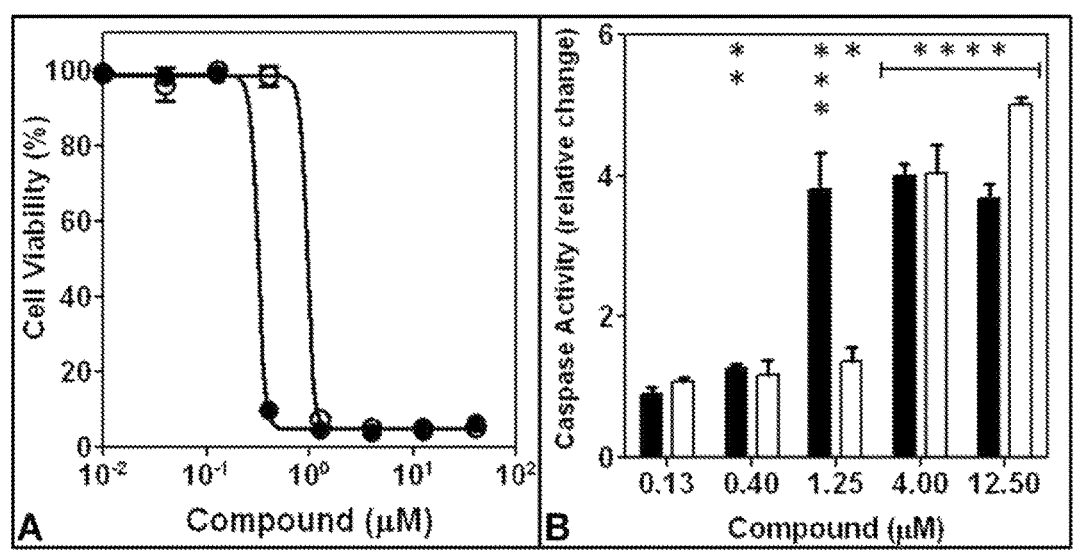
FIG. 7 graphically shows: A. cellular efficacy ($EC_{50}$, μM) of Compound A (filled circle) and Compound B (open circle) in a human VS HEI193 cell line. Cell viability was determined using the CellTiter-Glo assay (Promega), following the manufacturers' protocol; B. effects of Compound A and Compound B on caspase activity in HEI193 cell line. Caspase-3/7 activity was measured after treatment with Compound A (solid bar) or Compound B (open bar) for 48 hours using a Caspase Glo 3/7 assay kit (Promega). Statistical significance was determined using a one-tailed student's t test. : p>0.01; *: p<0.001; ****: p<0.0001.
Figure 8:
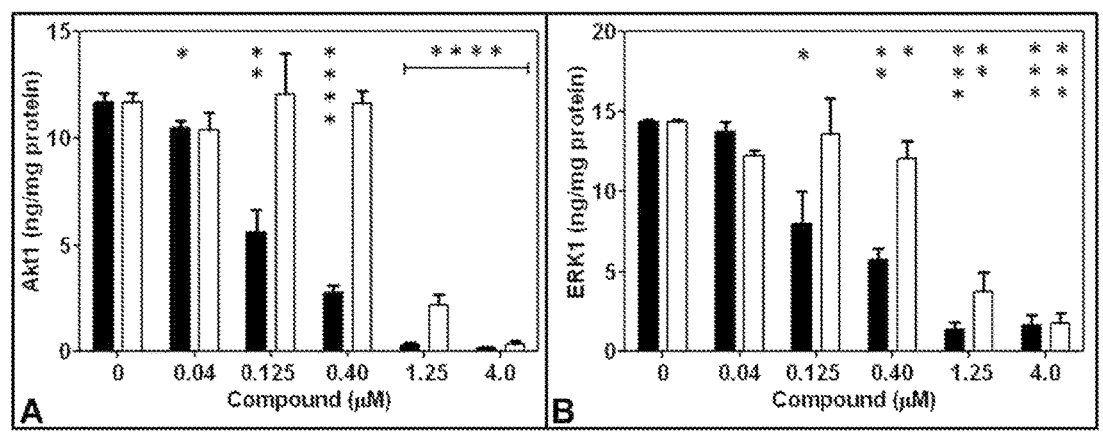

FIG. 8 graphically depicts in vitro pharmacodynamic effects and MOA of Compound A and Compound B showing reduction of Hsp90 client proteins in a clinically relevant human VS tumor cell model, HEI193. Akt1 (A) and ERK1 (B) levels were quantitated in cell lysates from HEI193 cells after a 48 hour treatment with Compound A (solid bar) or Compound B (open bar) using ELISA kits from R&D Systems. Statistical significance was determined as in FIG. 7.

Figure 9:
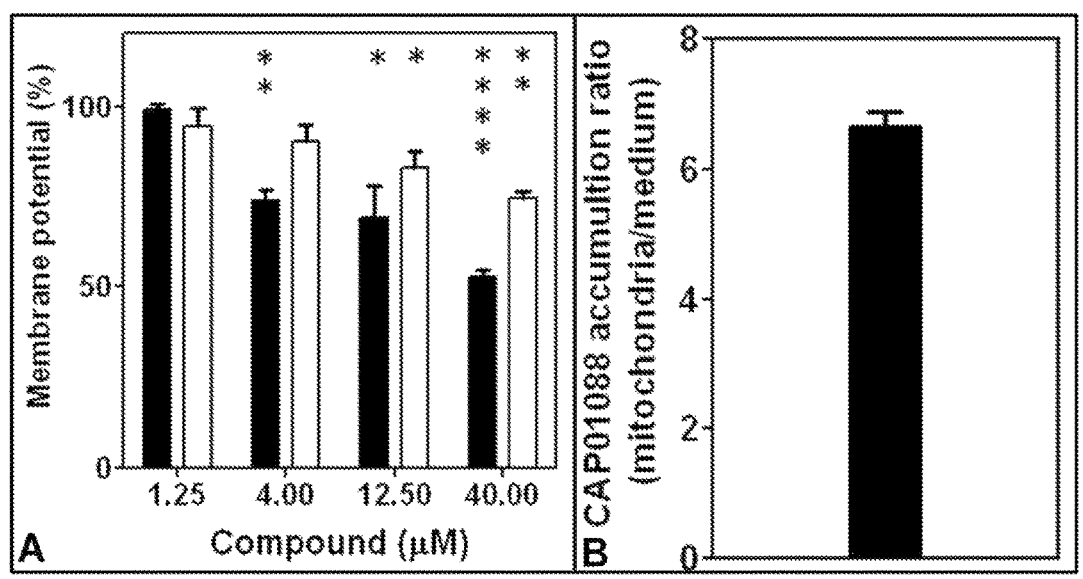

FIG. 9 shows graphically the effects of Hsp90/TRAP1i on HEI193 cell mitochondrial integrity. (A) Compound A (solid bar) causes a dose-dependent decrease in tetramethylrhodamine, ethyl ester (TMRE) fluorescence in HEI193 cells indicative of mitochondrial depolarization that was observed as early as 2 hours after treatment. Drug candidate, Ganetespib (open bar) produced a significantly weaker response at the same concentrations. (B) Compound A (20 uM) accumulated in mitochondria isolated from HEI193 cells to a level greater than 6-fold compared to that in culture medium. Data are mean±SEM of triplicate samples from two independent experiments. Statistical significance was determined as in FIG. 4.

Figure 10:
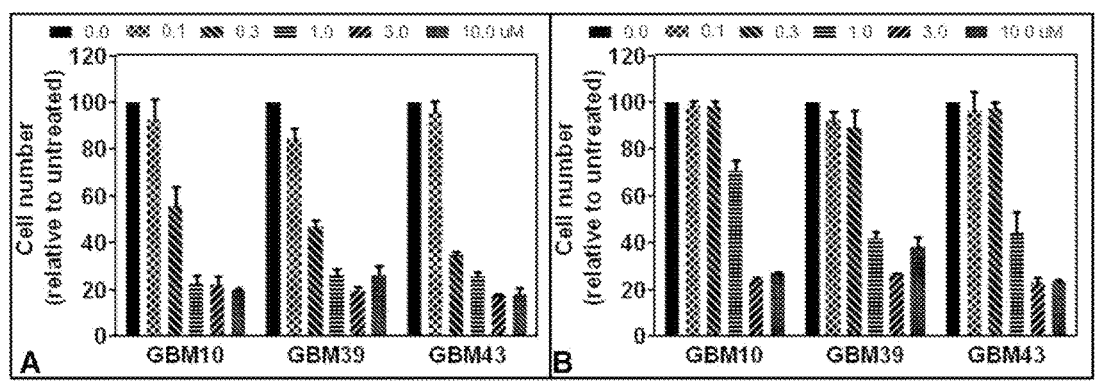

FIG. 10 graphically shows that Compound A and Compound B inhibit Mayo Clinic patient derived GBM tumor cell proliferation. GBM cell lines were treated for 132 hours with indicated concentrations of Compound A (A) & Compound B (B). The ±SD values for three independent experiments are shown in the graph, representing the percentage of viable cells relative to untreated conditions.

Figure 11:
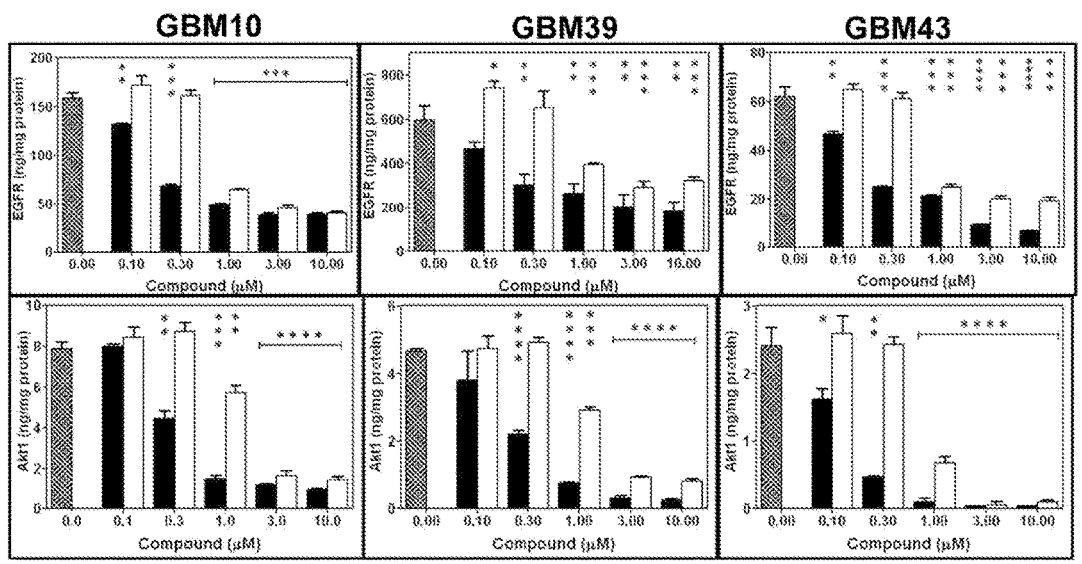

FIG. 11 depicts in a series of bar graph the in vitro pharmacodynamic effects of Compound A and Compound B showing suppression of Hsp90 client proteins in clinically relevant Mayo Clinic GBM PDX cell lines. EGFR and Akt1 levels were quantitated in cell lysates from three Mayo Clinic GBM PDX cells lines after treatment with no drug (checkered bar) or Compound A (solid bar) or Compound B (open bar) for 48 hours using ELISA kits from R&D Systems.

Figure 12:
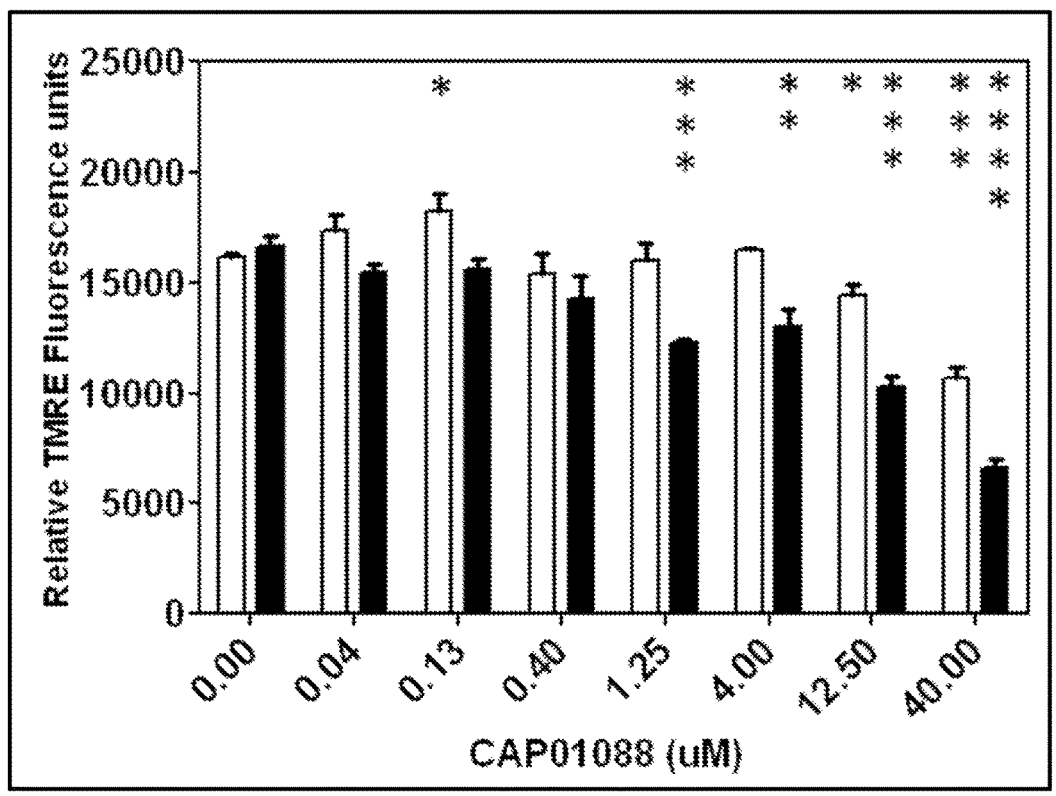

FIG. 12 shows in a bar graph that Compound A also caused a dose-dependent decrease in TMRE fluorescence of U251MG cells indicative of mitochondrial dysfunction, 2 hour (open bar) or 4 hr (solid bar).

DETAILED DESCRIPTION OF CERTAIN EMBODIMENTS

General Description of Compounds

In certain embodiments, the present disclosure provides a compound of Formula (I):

(I)

or a pharmaceutically acceptable salt thereof, wherein
$R^1$ is hydrogen, halo, $(C_1-C_3)$alkyl, halo$(C_1-C_3)$alkyl, $(C_1-C_3)$alkoxy, or halo$(C_1-C_3)$alkoxy;
$R^3$, $R^4$ and $R^5$ are each independently hydrogen, halo, $(C_1-C_3)$alkyl, halo $(C_1-C_3)$alkyl, $(C_1-C_3)$alkoxy, halo $(C_1-C_3)$alkoxy, cyano, $$-\overset{O}{\underset{\|}{C}}-N(R^7)(R^8), \quad -NH\overset{O}{\underset{\|}{C}}-R^9,$$

$R^2$ is heteroaryl, cycloalkyl, or heterocycyl, each of which are optionally substituted with 1 to 2 groups independently selected from $R^6$;
p is 0, 1, or 2;
each $R^6$ is independently selected from halo, cyano, nitro, amino, hydroxy, carboxy, $(C_1-C_6)$alkyl, aryl, heteroaryl, heteroarylalkyl, arylalkyl, heterocyclyl, hydroxy$(C_1-C_6)$alkyl, $CO_2H$, $(CH_2)_{1-3}COOH$, $(C_1-C_3)$alkylcarbonyloxy, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkythio, $(C_4-C_7)$cycloalkylalkylthio, halo$(C_1-C_6)$alkylthio, halo$(C_3-C_6)$cycloalkythio, halo$(C_4-C_7)$cycloalkylalkylthio, $(C_1-C_6)$alkylsulfinyl, $(C_3-C_6)$cycloalkylsulfinyl, $(C_4-C_7)$cycloalkylalkylsulfinyl, halo$(C_1-C_6)$alkylsulfonyl, halo$(C_3-C_6)$cycloalkylsulfinyl, halo$(C_4-C_7)$cycloalkylalkylsulfinyl, $(C_1-C_6)$alkylsulfonyl, $(C_3-C_6)$cycloalkylsulfonyl, $(C_4-C_7)$cycloalkylalkylsulfonyl, halo $(C_1-C_6)$alkylsulfonyl, halo$(C_3-C_6)$cycloalkylsulfonyl, halo $(C_4-C_7)$cycloalkylalkylsulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclylsulfonyl, $(C_1-C_6)$alkylcarbonylamino, $(C_1-C_6)$alkylcarbonylamino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, aryl, heteroaryl, oxo, amino$(C_1-C_6)$alkyl, $(C_1-C_6)$alkylamino$(C_1-C_6)$alkyl, di$(C_1-C_6)$alkylamino$(C_1-C_6)$alkyl amino$(C_2-C_6)$alkoxy, $(C_1-C_6)$alkylamino$(C_2-C_6)$alkoxy, di$(C_1-C_6)$alkylamino$(C_2-C_6)$alkoxy, $(C_1-C_6)$alkylcarbonyl, hydroxy$(C_1-C_6)$alkylcarbonyl, $(C_1-C_6)$alkylhydroxycarbonyl, $(C_1-C_6)$alkylhydroxy$(C_1-C_6)$alkyl, $(C_3-C_6)$cycloalkylcarbonyl, $(C_3-C_6)$cycloalkylaminocarbonyl, $(C_3-C_6)$cycloalkyl {$(C_1-C_6)$alkyl}aminocarbonyl, di$(C_3-C_6)$cycloalkylaminocarbonyl, $(C_3-C_6)$cycloalkylaminosulfonyl, {$(C_3-C_6)$cycloalkyl}{$(C_1-C_6)$alkyl}aminosulfonyl, di$(C_3-C_6)$cycloalkylaminosulfonyl, cyano$(C_1-C_6)$alkyl, aminocarbonyl$(C_1-C_6)$alkyl, $(C_1-C_6)$alkylaminocarbonyl$(C_1-C_6)$alkyl, di$(C_1-C_6)$alkylaminocarbonyl$(C_1-C_6)$alkyl, $(C_3-C_6)$cycloalkylaminocarbonyl$(C_1-C_6)$alkyl, {$(C_3-C_6)$cycloalkyl}{$(C_1-C_6)$alkyl}aminocarbonyl$(C_1-C_6)$alkyl, [$(C_1-C_6)$alkyl$(C_4-C_6)$heterocyclyl]$(C_1-C_6)$alkyl, and di$(C_3-C_6)$cycloalkylaminocarbonyl$(C_1-C_6)$alkyl; $R^7$ and $R^8$ are independently hydrogen or alkyl, e.g., $(C_1-C_3)$alkyl, $R^9$ is H or alkyl, e.g., $(C_1-C_3)$alkyl.

2. Compounds and Definitions

The terms "halo" and "halogen" as used herein refer to an atom selected from fluorine (fluoro, —F), chlorine (chloro, —Cl), bromine (bromo, —Br), and iodine (iodo, —I).

The term "alkyl", used alone or as a part of a larger moiety such as e.g., "haloalkyl", means a saturated monovalent straight or branched hydrocarbon radical having, unless otherwise specified, 1-10 carbon atoms and includes, for example, methyl, ethyl, n-propyl, isopropyl, n-butyl, sec-butyl, isobutyl, tert-butyl, n-pentyl, n-hexyl, n-heptyl, n-octyl, n-nonyl, n-decyl and the like. "Monovalent" means attached to the rest of the molecule at one point.

The terms "cycloalkyl" used alone or as part of a larger moiety, refers to a saturated cyclic aliphatic monocyclic or bicyclic ring system, as described herein, having from, unless otherwise specified, 3 to 10 carbon ring atoms. Monocyclic cycloalkyl groups include, without limitation, cyclopropyl, cyclobutyl, cyclopentyl, cyclopentenyl, cyclohexyl, cyclohexenyl, cycloheptyl, cycloheptenyl, and cyclooctyl. Bicyclic cycloalkyl groups include e.g., cycloalkyl group fused to another cycloalkyl group, such as decalin or a cycloalkyl group fused to an aryl group (e.g., phenyl) or heteroaryl group, such as tetrahydronaphthalenyl, indanyl, 5,6,7,8-tetrahydroquinoline, and 5,6,7,8-tetrahydroisoquinoline. It will be understood that the point of attachment for bicyclic cycloalkyl groups can be either on the cycloalkyl portion or on the aryl group (e.g., phenyl) or heteroaryl group that results in a stable structure. It will be further understood that when specified, optional substituents on a cycloalkyl may be present on any substitutable position and, include, e.g., the position at which the cycloalkyl is attached.

The term "heterocyclyl" means a 4-, 5-, 6- and 7-membered saturated or partially unsaturated heterocyclic ring containing 1 to 4 heteroatoms independently selected from N, O, and S. The terms "heterocycle", "heterocyclyl", "heterocyclyl ring", "heterocyclic group", "heterocyclic moiety", and "heterocyclic radical", may be used interchangeably. A heterocyclyl ring can be attached to its pendant group at any heteroatom or carbon atom that results in a stable structure. Examples of such saturated or partially unsaturated heterocyclic radicals include, without limitation, tetrahydrofuranyl, tetrahydrothienyl, terahydropyranyl, pyrrolidinyl, pyrrolidonyl, piperidinyl, oxetanyl, oxazolidinyl, piperazinyl, dioxanyl, dioxolanyl, morpholinyl, dihydrofuranyl, dihydropyranyl, dihydropyridinyl, tetrahydropyridinyl, dihydropyrimidinyl, and tetrahydropyrimidinyl. A heterocyclyl group may be mono- or bicyclic. Unless otherwise specified, bicyclic heterocyclyl groups include, e.g., unsaturated or saturated heterocyclic radicals fused to another unsaturated heterocyclic radical or aromatic or heteroaryl ring, such as for example, chromanyl, 2,3-dihydrobenzo[b][1,4]dioxinyl, tetrahydronaphthyridinyl, indolinonyl, dihydropyrrolotriazolyl, imidazopyrimidinyl, quinolinonyl, dioxaspirodecanyl. It will be understood that the point of attachment for bicyclic heterocyclyl groups can be on the heterocyclyl group or aromatic ring that results in a stable structure. It will also be understood that when specified, optional substituents on a heterocyclyl group may be present on any substitutable position and, include, e.g., the position at which the heterocyclyl is attached.

The term "heteroaryl" used alone or as part of a larger moiety as in "heteroarylalkyl", "heteroarylalkoxy", or "heteroarylaminoalkyl", refers to a 5-10-membered aromatic radical containing 1-4 heteroatoms selected from N, O, and S and includes, for example, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The term "heteroaryl" may be used interchangeably with the terms "heteroaryl ring", "heteroaryl group", or "heteroaromatic". The terms "heteroaryl" and "heteroar-", as used herein, also include groups in which a heteroaromatic ring is fused to one or more aryl rings, where the radical or point of attachment is on the heteroaromatic ring. Nonlimiting examples include indolyl, indazolyl, benzimidazolyl, benzthiazolyl, quinolyl, quinazolinyl, and quinoxalinyl. A heteroaryl group may be mono- or bicyclic. It will be understood that when specified, optional substituents on a heteroaryl group may be present on any substitutable position and, include, e.g., the position at which the heteroaryl is attached.

As used herein, the term "aryl", used alone or in conjunction with other terms, refers to a 6-14 membered aromatic ring containing only ring carbon atoms. The aryl ring may be monocyclic, bicyclic or tricyclic. Non-limiting examples include phenyl, naphthyl or anthracenyl, and the like. It will also be understood that when specified, optional substituents on an aryl group may be present on any substitutable position. In an embodiment, the aryl group is unsubstituted or mono- or di-substituted.

The term oxane, as used herein, is synonymous with tetrahydropyran, and both are used interchangeably herein.

As used herein the terms "subject" and "patient" may be used interchangeably, and means a mammal in need of treatment, e.g., companion animals (e.g., dogs, cats, and the like), farm animals (e.g., cows, pigs, horses, sheep, goats and the like) and laboratory animals (e.g., rats, mice, guinea pigs and the like). Typically, the subject is a human in need of treatment.

The compounds of the invention may be present in the form of pharmaceutically acceptable salts. For use in medicines, the salts of the compounds of the invention refer to non-toxic "pharmaceutically acceptable salts." Pharmaceutically acceptable salt forms include pharmaceutically acceptable acidic/anionic or basic/cationic salts.

Pharmaceutically acceptable basic/cationic salts include, the sodium, potassium, calcium, magnesium, diethanolamine, n-methyl-D-glucamine, L-lysine, L-arginine, ammonium, ethanolamine, piperazine and triethanolamine salts.

Pharmaceutically acceptable acidic/anionic salts include, e.g., the acetate, benzenesulfonate, benzoate, bicarbonate, bitartrate, carbonate, citrate, dihydrochloride, gluconate, glutamate, glycollylarsanilate, hexylresorcinate, hydrobromide, hydrochloride, malate, maleate, malonate, mesylate, nitrate, salicylate, stearate, succinate, sulfate, tartrate, and tosylate.

3. Description of Exemplary Compounds

In a first embodiment, the present disclosure provides a compound of Formula (I):

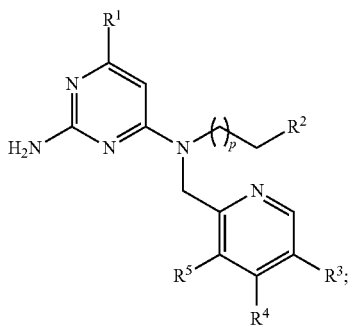

or a pharmaceutically acceptable salt thereof, wherein the variables are as described above.

In a second embodiment, the compound of Formula (I) is of the Formula (II):

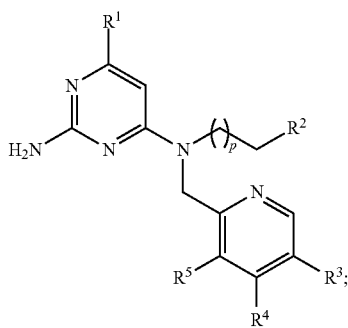

or a pharmaceutically acceptable salt thereof, wherein the variables are as described above for Formula (I), except that p is 0 or 1. In an embodiment, p is 0 when $R^2$ is oxane. In another embodiment, p is 1 when $R^2$ is pyridyl.

In a third embodiment, $R^1$ in Formula (I) or Formula (II) is halo, wherein the remainder of the variables are as described in Formula (I), except that p is 0 or 1. In an embodiment, p is 0 when $R^2$ is oxane. In another embodiment, p is 1 when $R^2$ is pyridyl.

In a fourth embodiment, $R^1$ in Formula (I) or Formula (II) is chloro, wherein the remainder of the variables are as described in Formula (I) or the third embodiment, except that p is 0 or 1. In an embodiment, p is 0 when $R^2$ is oxane. In another embodiment, p is 1 when $R^2$ is pyridyl.

In a fifth embodiment, $R^3$, $R^4$, and $R^5$ in Formula (I) or Formula (II) are each independently $(C_1-C_3)$alkyl or $(C_1-C_3)$alkoxy, cyano, carboxy,

N-methylamide, or acetylamino wherein the remainder of the variables are as described in Formula (I) or the third or fourth embodiment, except that p is 0 or 1. In an embodiment, p is 0 when $R^2$ is oxane. In another embodiment, p is 1 when $R^2$ is pyridyl.

In a sixth embodiment, $R^3$ and $R^5$ in Formula (I) or Formula (II) are each $(C_1-C_3)$alkyl; and $R^4$ is $(C_1-C_3)$alkoxy, wherein the remainder of the variables are as described in Formula (I) or the third, forth, or fifth embodiment, except that p is 0 or 1. In an embodiment, p is 0 when $R^2$ is oxane. In another embodiment, p is 1 when $R^2$ is pyridyl.

In a seventh embodiment, $R^3$ and $R^5$ in Formula (I) or Formula (II) are each methyl; and $R^4$ is methoxy, wherein the remainder of the variables are as described in Formula (I) or the third, fourth, fifth, or sixth embodiment, except that p is 0 or 1. In an embodiment, p is 0 when $R^2$ is oxane. In another embodiment, p is 1 when $R^2$ is pyridyl.

In an eighth embodiment, $R^2$ in Formula (I) or Formula (II) is heteroaryl, which may be monocyclic or bicyclic; hetrerocyclic, which may be monocyclic or bicyclic, each of which are optionally substituted with 1 to 2 groups independently selected from $R^6$, wherein the remainder of the variables are as described in Formula (I) or the third, fourth, fifth, sixth, or seventh embodiment, except that p is 0 or 1. In an embodiment, p is 0 when $R^2$ is oxane. In another embodiment, p is 1 when $R^2$ is pyridyl.

In a ninth embodiment, $R^2$ in Formula (I) or Formula (II) is pyridyl, pyrazinyl, tetrahydronaphthalenyl, tetrahydroquinolinyl, 2,3-dihydrobenzo[b][1,4]dioxinyl, or chromanyl, tetrahydrofuryl, dihydrofuryl, furyl, oxanyl, dihyropyranyl or pyranyl, each of which are optionally substituted with 1 to 2 groups independently selected from $R^6$, wherein the remainder of the variables are as described in Formula (I) or the third, fourth, fifth, sixth, seventh, or eighth embodiment, except that p is 0 or 1. In an embodiment, p is 0 when $R^2$ is oxane. In another embodiment, p is 1 when $R^2$ is pyridyl.

In a tenth embodiment, $R^2$ in Formula (I) or Formula (II) is pyridyl, pyrazinyl-2-yl, chroman-2-yl, chroman-3-yl, chroman-6-yl, chroman-7-yl, 2,3-dihydrobenzo[b][1,4]dioxine-2-yl, 2,3-dihydrobenzo[b][1,4]dioxine-6-yl, 5,6,7,8-tetrahydroquinolin-7-yl, 1,2,3,4-tetrahydronaphthalen-6-yl, 1,2,3,4-tetrahydronaphthalen-2-yl, furyl, oxan-2-yl, oxan-3-yl, oxan-4-yl, 3,4-dihydro-2H-pyran-2-yl. 3,4-dihydro-2H-pyran-3-yl, 3,4-dihydro-2H-pyran-4-yl, pyran-1-yl, pyran-2-yl, pyran-3-yl, 1-tetrahydrofuryl, 2-tetrahydrofuryl, 3-tetrdihyrofuryl, each of which are optionally substituted with 1 to 2 groups independently selected from $R^6$, wherein the remainder of the variables are as described in Formula (I) or the third, fourth, fifth, sixth, seventh, eighth, or ninth embodiment, except that p is 0 or 1. In an embodiment, p is 0 when $R^2$ is oxane. In another embodiment, p is 1 when $R^2$ is pyridyl.

In an eleventh embodiment, $R^6$ in Formula (I) or Formula (II) is selected from halo, $(C_1-C_3)$alkyl, halo$(C_1-C_3)$alkyl, $(C_1-C_3)$alkoxy, and halo$(C_1-C_3)$alkoxy, wherein the remainder of the variables are as described in Formula (I) or the third, fourth, fifth, sixth, seventh, eighth, ninth, or tenth embodiment, except that p is 0 or 1. In an embodiment, p is 0 when $R^2$ is oxane. In another embodiment, p is 1 when $R^2$ is pyridyl.

In a twelfth embodiment, $R^2$ in Formula (I) or Formula (II) is pyridyl or oxanyl, wherein each is optionally substituted with 1 to 2 groups selected from halo, $(C_1-C_3)$alkyl, halo$(C_1-C_3)$alkyl, $(C_1-C_3)$alkoxy, and halo$(C_1-C_3)$alkoxy, wherein the remainder of the variables are as described in Formula (I) or the third, forth, fifth, sixth, seventh, eighth, ninth, tenth, or eleventh embodiment, except that p is 0 or 1. In an embodiment, p is 0 when $R^2$ is oxane. In another embodiment, p is 1 when $R^2$ is pyridyl.

In a thirteenth embodiment, $R^2$ in Formula (I) or Formula (II) is unsubstituted pyridyl or oxanyl, wherein the remainder of the variables are as described in Formula (I) or the third, forth, fifth, sixth, seventh, eighth, ninth, tenth, eleventh, or twelfth embodiment, except that p is 0 or 1. In an embodiment, p is 0 when $R^2$ is oxane. In another embodiment, p is 1 when $R^2$ is pyridyl.

In a fourteenth embodiment, $R^2$ in Formula (I) or Formula (II) is pyridyl, pyrrole, or the dihydro- or tetrahydro derivatives of pyrrole or or pyridyl or is pyran or furan or dihydrofuran or dihydropyran or oxane or tetrahydrofuran. The $R^2$ group is optionally substituted with 1 to 2 groups selected from halo, $(C_1-C_3)$alkyl, halo$(C_1-C_3)$alkyl, $(C_1-C_3)$alkoxy, and halo$(C_1-C_3)$alkoxy, wherein the remainder of the variables are as described in Formula (I) or the third, fourth, fifth, sixth, seventh, eighth, ninth, tenth, or eleventh embodiment, except that p is 0 or 1. In an embodiment, p is 0 when $R^2$ is oxane. In another embodiment, p is 1 when $R^2$ is pyridyl.

In the various embodiments, the nitrogen ring heteroatom and the oxygen ring heteroatom in the aforesaid moieties may be on any position of the ring. When $R^2$ is heterocyclic the position to which the N—$(CH_2)_p CH_2$ group and $R^6$ is attached may be on the same carbon atom of the heterocyclic ring. However, it is understood that each carbon atom 4 bonds attached to it. Thus, the nitrogen atom in the nitrogen containing moieties described in this paragraph may be in the 1, 2-, or 3-position of the 5-membered ring or the 1, 2- or 3- or 4-position of the 6-membered ring. Similarly, the oxygen ring atom may be in the 1, 2-, or 3-position of the 5-membered ring or the 1, 2- or 3- or 4-position of the 6-membered ring.

In a fifteenth embodiment, $R^2$ in Formula (I) or Formula (II) is pyridyl or pyrrole, or tetrahydrofuran or oxane, which $R^2$ may be optionally substituted with 1 to 2 groups selected from halo, $(C_1-C_3)$alkyl, halo$(C_1-C_3)$alkyl, $(C_1-C_3)$alkoxy, and halo$(C_1-C_3)$alkoxy, wherein the remainder of the variables are as described in Formula (I) or the third, fourth, fifth, sixth, seventh, eighth, ninth, tenth, or eleventh embodiment, except that p is 0 or 1. In an embodiment, p is 0 when $R^2$ is oxane. In another embodiment, p is 1 when $R^2$ is pyridyl.

In a sixteenth embodiment, the compound of Formula (I) is of Formula (III):

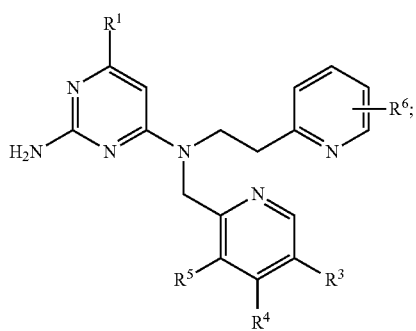

(III)

or a pharmaceutically acceptable salt thereof, wherein
$R^1$ is halo;
$R^3$ and $R^5$ are $(C_1-C_3)$alkyl;
$R^4$ is $(C_1-C_3)$alkoxy; and
$R^6$ is selected from hydrogen, halo, $(C_1-C_3)$alkyl, halo$(C_1-C_3)$alkyl, $(C_1-C_3)$alkoxy, and halo$(C_1-C_3)$alkoxy.

In a seventeenth embodiment, $R^6$ in Formula (III) is hydrogen, wherein the remaining variables are as described for Formula (III).

In an eighteenth embodiment, the compound of Formula (I) is of Formula (IV):

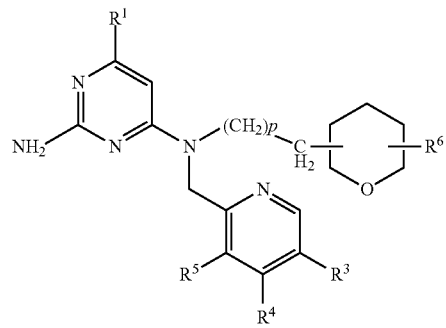

IV or pharmaceutically acceptable salts wherein, $R^1$, $R^3$, $R^4$, $R^5$, $R^6$ and p are as defined hereinabove in any of the aforementioned embodiments. It is understood that in the formula hereinabove, $R^6$ and $N(CH_2)pCH_2$ moieties may be substituted on different carbon atoms of the oxanyl ring or on the same carbon atom of the oxanyl ring.

For example, in an embodiment, the compound is of Formula IV, wherein $R^1$, $R^3$, $R^4$, and $R^5$ are as defined in any one of the aforesaid embodiments.

In another embodiment, $R^1$, $R^3$, $R^4$, and $R^5$ are each independently hydrogen, halo, $(C_1-C_3)$alkyl, halo$(C_1-C_3)$alkyl, $(C_1-C_3)$alkoxy, or halo$(C_1-C_3)$alkoxy, and $R^6$ is selected from hydrogen, alkyl, aryl, which is unsubstituted or substituted with halo, alkyl, or haloalkyl, or a 5 or 6-membered heteroaryl, containing nitrogen as the only ring heteroatom.

In another embodiment, the compound is of Formula (IV), wherein
$R^1$ is halo;
$R^3$ and $R^5$ are $(C_1-C_3)$alkyl;
$R^4$ is $(C_1-C_3)$alkoxy; and
$R^6$ is selected from hydrogen, alkyl, pyridyl, which may be unsubstituted or substituted with alkyl, or halo, or phenyl, which may be unsubstituted or substituted with halo or alkyl.

In a further embodiment, the compound is of Formula (IV), where $R^6$ in Formula-(IV) is hydrogen, 4-fluorophenyl, 2-pyridyl, or 5-methyl-2-pyridyl, wherein the remaining variables are as described for Formula (IV).

In a further embodiment, the compound is of Formula IV where p is 0, wherein $R^1$, $R^3$, $R^4$, and $R^5$ are as defined in any one of the aforesaid embodiments.

In a further embodiment, the compound is of Formula IV, where p is 0, $R^1$, $R^3$, $R^4$, and $R^5$ are each independently hydrogen, halo, $(C_1-C_3)$alkyl, halo$(C_1-C_3)$alkyl, $(C_1-C_3)$alkoxy, or halo$(C_1-C_3)$alkoxy, and $R^6$ is selected from hydrogen, aryl, which is unsubstituted or substituted with halo, alkyl, or haloalkyl, or a 5 or 6-membered heteroaryl, containing nitrogen as the only ring heteroatom.

In another embodiment, the compound is of Formula (IV), wherein p is 0,
$R^1$ is halo;
$R^3$ and $R^5$ are $(C_1-C_3)$alkyl;
$R^4$ is $(C_1-C_3)$alkoxy; and
$R^6$ is selected from pyridyl, which may be unsubstituted or substituted with alkyl, or halo, or phenyl, which may be unsubstituted or substituted with halo or alkyl, or $R^6$ is hydrogen.

In a still further embodiment, the compound is of Formula (IV), wherein $R^6$ in Formula (IV) is 4-fluorophenyl, 2-pyridyl, or 5-methyl-2-pyridyl, wherein the remaining variables are as described for Formula (IV) and p is 0.

In another embodiment, the compound is of Formula (V)

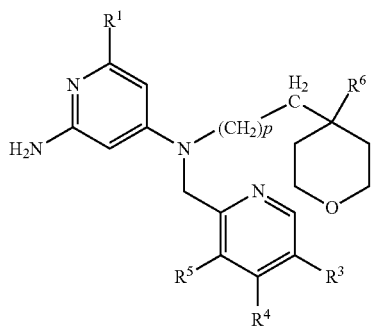

or pharmaceutically acceptable salts thereof wherein $R^1$, $R^3$, $R^4$, and $R^5$ and p are as defined herein any of the aforementioned embodiments.

In another embodiment, the compound of Formula (V) wherein p is 0.

In a further embodiment, the compound is of Formula IV where p is 0, wherein $R^1$, $R^3$, $R^4$, and $R^5$ are as defined in any one of the aforesaid embodiments.

In a further embodiment, the compound is of Formula IV, where p is 0, $R^1$, $R^3$, $R^4$, and $R^5$ are each independently hydrogen, halo, $(C_1-C_3)$alkyl, halo$(C_1-C_3)$alkyl, $(C_1-C_3)$alkoxy, or halo$(C_1-C_3)$alkoxy, and $R^5$ is selected from aryl, which is unsubstituted or substituted with halo, alkyl, or haloalkyl, or a 5 or 6-membered heteroaryl, containing nitrogen as the only ring heteroatom.

In another embodiment, the compound is of Formula (IV), wherein p is 0, $R^1$ is halo;

$R^3$ and $R^5$ are $(C_1-C_3)$alkyl;

$R^4$ is $(C_1-C_3)$alkoxy; and $R^6$ is selected from hydrogen, pyridyl, which may be unsubstituted or substituted with alkyl, or halo, or phenyl, which may be unsubstituted or substituted with halo or alkyl.

In a still further embodiment, the compound is of Formula (IV), wherein $R^6$ in Formula (IV) is hydrogen, 4-fluorophenyl, 2-pyridyl, or 5-methyl-2-pyridyl, wherein the remaining variables are as described for Formula (IV) and p is 0.

Specific examples of compounds of the disclosure are provided in the EXEMPLIFICATION. Pharmaceutically acceptable salts as well as the neutral forms of these compounds are included in the present disclosure.

In certain embodiments, the present disclosure provides any one of the compounds of the foregoing or examples later described, or a pharmaceutically acceptable salt thereof.

In certain embodiments, the present disclosure provides a method of treating a patient (e.g., a human) with a cancer mediated by Hsp90/TRAP1 comprising the step of administering to the patient an effective amount of the compound with any compound described herein, or a pharmaceutically acceptable salt or composition thereof.

4. Uses, Formulation and Administration

Pharmaceutically Acceptable Compositions

According to another embodiment, the present disclosure provides a method of treating a subject (e.g., a human) with a cancer mediated by Hsp90/TRAP1 using a composition comprising a compound of Formula (I) and a pharmaceutically acceptable carrier, adjuvant, or vehicle. In certain embodiments, the amount of compound of Formula (I) in a provided composition is such that it is effective as a dual inhibitor of Hsp90/TRAP1 in a biological sample or in a subject. In certain embodiments, a provided composition is formulated for administration to a subject in need of such composition. In some embodiments, a provided composition is formulated for oral administration to a subject.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this disclosure include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Remington's Pharmaceutical Sciences Ed. by Gennaro, Mack Publishing, Easton, Pa., 1995 (the contents of which are hereby incorporated by reference), discloses various carriers used in formulating pharmaceutical compositions and known techniques for the preparation thereof.

Compositions described herein may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a provided compound, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

Provided compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents.

They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Pharmaceutically acceptable compositions provided herein may be formulated for oral administration. Such formulations may be administered with or without food. In some embodiments, pharmaceutically acceptable compositions of this disclosure are administered without food. In other embodiments, pharmaceutically acceptable compositions of this disclosure are administered with food.

The amount of provided compounds that may be combined with carrier materials to produce a composition in a single dosage form will vary depending upon the patient to be treated and the particular mode of administration.

It should also be understood that a specific dosage and treatment regimen for any particular patient will depend upon a variety of factors, including age, body weight, general health, sex, diet, time of administration, rate of excretion, drug combination, the judgment of the treating physician, and the severity of the particular disease being treated. The amount of a provided compound in the composition will also depend upon the particular compound in the composition.

Uses of Compounds and Pharmaceutically Acceptable Compositions

Compounds and compositions described herein are generally useful for the dual inhibition of Hsp90/TRAP1. Thus, in some embodiments, the present disclosure provides a method of treating cancer, comprising administering a provided compound or composition.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed, i.e., therapeutic treatment. In other embodiments, treatment may be administered in the absence of symptoms. For example, treatment may be administered to a susceptible individual prior to the onset of symptoms (e.g., in light of a history of symptoms and/or in light of genetic or other susceptibility factors), i.e., prophylactic treatment. Treatment may also be continued after symptoms have resolved, for example to prevent or delay their recurrence.

The term "cancer" or "tumor" are well known in the art and refer to the presence, e.g., in a subject, of cells possessing characteristics typical of cancer-causing cells, such as uncontrolled proliferation, immortality, metastatic potential, rapid growth and proliferation rate, decreased cell death/apoptosis, and certain characteristic morphological features. As used herein, "cancer" or "tumor" refers to all types of cancer or neoplasm or malignant tumors found in humans, including, but not limited to: leukemias, lymphomas, melanomas, carcinomas and sarcomas. As used herein, the terms "cancer," "neoplasm," and "tumor," are used interchangeably and in either the singular or plural form, refer to cells that have undergone a malignant transformation that makes them pathological to the host organism. Primary cancer cells (that is, cells obtained from near the site of malignant transformation) can be readily distinguished from non-cancerous cells by well-established techniques, particularly histological examination. The definition of a cancer cell, as used herein, includes not only a primary cancer cell, but also cancer stem cells, as well as cancer progenitor cells or any cell derived from a cancer cell ancestor. This includes metastasized cancer cells, and in vitro cultures and cell lines derived from cancer cells.

In certain embodiments cancers treatable according to the methods described herein include a carcinoma, sarcoma, lymphoma, melanoma, and leukemia. In one embodiment, the treatable cancers include pancreatic cancer, breast cancer, liver cancer, skin cancer, lung cancer, colon cancer, prostate cancer, thyroid cancer, bladder cancer, rectal cancer, endometrial cancer, kidney cancer, bone cancer, brain cancer (e.g. glioblastoma multiforme), cervical cancer, stomach cancer, mouth and oral cancers, neuroblastoma, testicular cancer, uterine cancer, and vulvar cancer. In a further embodiment, the skin cancer is selected from the group consisting of melanoma, squamous cell carcinoma, basal cell carcinoma, and cutaneous T-cell lymphoma (CTCL). In another embodiment, the oncological disorder is triple negative breast cancer.

The term "sarcoma" generally refers to a tumor which is made up of a substance like the embryonic connective tissue and is generally composed of closely packed cells embedded in a fibrillar or homogeneous substance. Examples of sarcomas which can be treated with a colloidal dispersion of CoQ10 in an IV formulation include, for example, a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma.

The term "melanoma" is taken to mean a tumor arising from the melanocytic system of the skin and other organs. Melanomas which can be treated with the colloidal dispersions of CoQ10 in IV formulation include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, and superficial spreading melanoma.

The term "carcinoma" refers to a malignant new growth made up of epithelial cells tending to infiltrate the surrounding tissues and give rise to metastases. Carcinomas which can be treated with the colloidal dispersions of CoQ10 in IV formulation, as described herein, include, for example, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniform carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypemephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, merkel cell carcinoma, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, and carcinoma villosum.

The disclosure further relates to a combination therapy for treating or ameliorating a cancer described herein. In some embodiments, the combination therapy comprises administering at least one compound represented by Formula I in combination with one or more agents selected from the group consisting of growth factors, anti-inflammatory agents, vasopressor agents, collagenase inhibitors, topical steroids, matrix metalloproteinase inhibitors, ascorbates, calreticulin, tetracyclines, fibronectin, collagen, thrombospondin, transforming growth factors (TGF), keratinocyte growth factor (KGF), fibroblast growth factor (FGF), insulin-like growth factors (IGF), epidermal growth factor (EGF), platelet derived growth factor (PDGF), neu differentiation factor (NDF), and hyaluronic acid.

The disclosure further provides a method of treating a subject, such as a human, suffering from one of the above-mentioned disorders or diseases.

The disclosure further relates to the use of provided compounds for the production of pharmaceutical compositions which are employed for the treatment and/or prophylaxis and/or amelioration of the diseases and disorders mentioned herein.

Compounds or compositions described herein may be administered using any amount and any route of administration effective for treating or lessening the severity of one or more of the cancers described herein. The exact amount required will vary from subject to subject, depending on the species, age, and general condition of the subject, the severity of the infection, the particular agent, its mode of administration, and the like. Provided compounds are preferably formulated in unit dosage form for ease of administration and uniformity of dosage. The expression "unit dosage form" as used herein refers to a physically discrete unit of agent appropriate for the patient to be treated. It will be understood, however, that the total daily usage of the compounds and compositions of the present disclosure will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. Pharmaceutically acceptable compositions of this disclosure can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, provided compounds may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

The term "biological sample", as used herein, includes, without limitation, cell cultures or extracts thereof, biopsied material obtained from a mammal or extracts thereof, and blood, saliva, urine, feces, semen, tears, or other body fluids or extracts thereof.

The amount of both, a provided compound and additional therapeutic agent (in those compositions which comprise an additional therapeutic agent as described above) that may be combined with the carrier materials to produce a single dosage form will vary depending upon the host treated and the particular mode of administration.

In those compositions which comprise an additional therapeutic agent, that additional therapeutic agent and the provided compound may act synergistically. Therefore, the amount of additional therapeutic agent in such compositions will be less than that required in a monotherapy utilizing only that therapeutic agent.

The amount of additional therapeutic agent present in the compositions of this disclosure will be no more than the amount that would normally be administered in a composition comprising that therapeutic agent as the only active agent.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

Compounds according to Formula (I) can be prepared by art recognized techniques. The following scheme I is exemplary. The final pyrimidine analogues as desired product. were obtained by reacting an intermediate compound of Formula (502) with appropriate chloropyrimidine-amine intermediate of Formula (503) in the presence of a suitable base, such as e.g., triethylamine under microwave irradiation at moderate temperature (e.g., 65° C.) in a polar aprotic solvent, such as, for example, dimethylformamide (DMF). Intermediate compound of Formula (502) can be prepared from reacting a compound of Formula (500) with an amine of the Formula (501), a reaction that is performed in a polar aprotic solvent, such as, for example, dimethylformamide (DMF), in the presence of a suitable base, such as, for example, N,N-diisopropylethylamine (DIPEA) by heating, such as under microwave irradiation (MW) at high temperature (e.g., 120° C.).

Scheme 1: PREPARATION OF COMPOUNDS OF FORMULA I

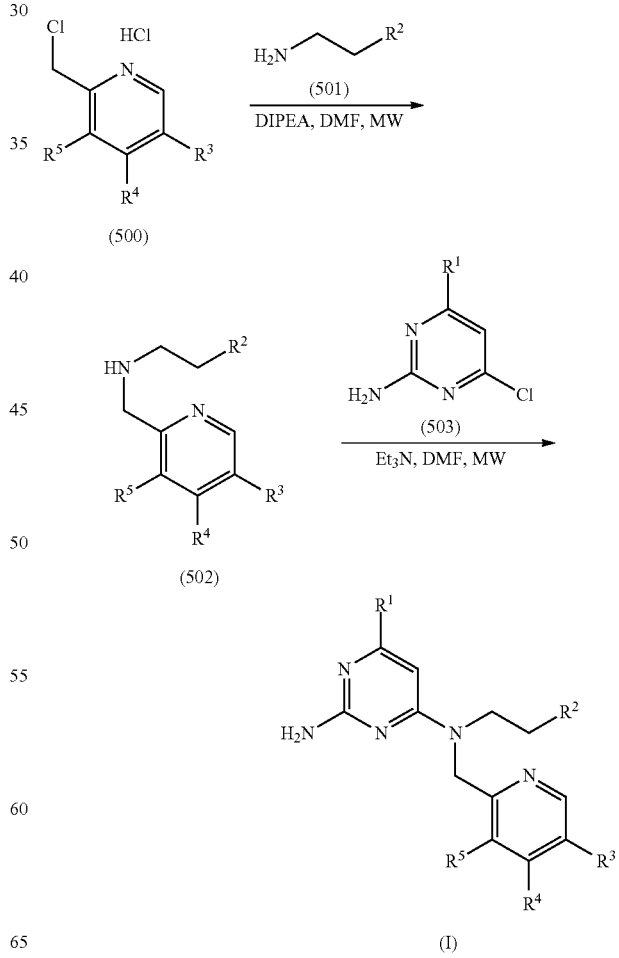

Compounds of Formula (I) were prepared according to the general procedures outlined below.

Example 1: 6-chloro-4-N-[(4-methoxy-3,5-dimethylpyridin-2yl)methyl]-4-N-[2-(pyridine-2-yl)ethyl]pyrimidine-2,4-amine (Compound 1)

(a)[(4-methoxy-3,5-dimethylpyridin-2-yl)methyl][2-(pyridin-2-yl)ethyl]amine

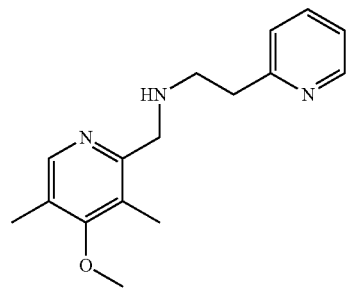 [SMILES: COc1c(C)cnc(CNCCc2ccccn2)c1C]

In a 10.0 mL brown glass vial, 2-(2-aminoethyl)-pyridine (488.8 mg, 4.0 mmol) was dissolved in DMF (2.0 mL), then added diisopropyl ethylamine (346.9 uL, 2.0 mmol). Then added 2-chloromethyl 3,5-dimethyl 4-methoxypyridine hydrochloride (222 mg, 1.0 mmol) to the reaction mixture, then closed the vial with cap and continued heating at 100° C. for 1.5 hours. Then washed the reaction mixture with water (10 mL) and extracted into dichloromethane (30 mL). Dried the organic layer over sodium sulfate and evaporated under reduced pressure. The resulted residue was purified on vacuum column chromatography using hexane-EtOAc (0-100%) and/or dichloromethane-methanol (0-20%) as solvent system. Pure product fractions were combined and evaporated to give [(4-methoxy-3,5-dimethylpyridin-2yl)methyl][2-(pyridin-2-yl)ethyl]amine as light yellow liquid (245 mg, 0.9 mmol, 90% yield). MS: m/z [M+H]$^+$ calculated for $C_{16}H_{21}N_3O$, 272; found 272.

(b) 6-chloro-4-N-[(4-methoxy-3,5-dimethylpyridin-2yl)methyl]-4-N-[2-(pyridine-2-yl)ethyl] pyrimidine-2,4-amine (Compound 1)

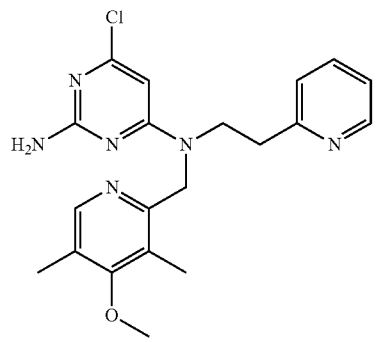 [SMILES: COc1c(C)cnc(CN(CCc2ccccn2)c2cc(Cl)nc(N)n2)c1C]

In a 10.0 mL brown glass vial, [(4-methoxy-3,5-dimethylpyridin-2yl)methyl][2-(pyridine-2-yl) ethyl]amine (136 mg, 0.5 mmol) was dissolved in ethanol (2.0 mL), then added triethylamine (140 uL, 1.0 mmol). Then added 2-amino 4,6-dichloropyrimidine (98 mg, 0.6 mmol) to the above mixture, then closed the vial with cap and heated at 100° C. for 5-10 hours. Evaporated the reaction mixture and washed with water (15 mL) extracted into dichloromethane (2×25 mL). Combined organic layer dried over sodium sulfate and evaporated. Then purified on vacuum column chromatography using hexane-EtOAc (0-100%) and/or dichloromethane-methanol (0-20%) as solvent system. Pure product fractions were combined and evaporated to give 6-chloro-4-N-[(4-methoxy-3,5-dimethylpyridin-2yl)methyl]-4-N-[2-(pyridine-2-yl)ethyl]pyrimidine-2,4-amine as tan solid (110 mg, 0.276 mmol, 55% yield). $^1$H NMR (CDCl3, 400 MHz): 8.51 (d, J=7.2 Hz, 1H), 8.16 (s, 1H), 7.56 (dt, J=6.4, 1.2 Hz, 1H), 7.11 (m, 2H), 5.94 (br s, 1H), 4.76 (br s, 4H), 3.81 (m, 2H), 3.74 (s, 3H), 3.03 (t, J=5.6 Hz, 2H), 2.22 (s, 3H), 2.17 (s, 3H); MS: m/z [M+H]$^+$ calculated for $C_{20}H_{23}ClN_6O$, 399; found 399.

Example 2: 6-chloro-4-N-{[4-(4-fluorophenyl)oxan-4-yl]methyl}-4-N-[(4-methoxy-3,5-dimethylpyridin-2-yl)methyl]pyrimidine-2,4-diamine (Compound A)

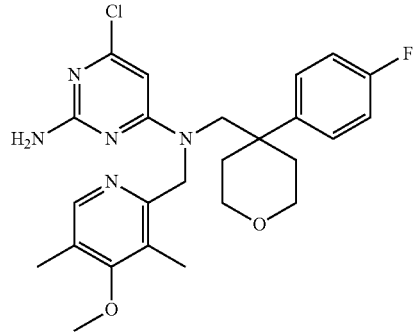 [SMILES: COc1c(C)cnc(CN(CC2(c3ccc(F)cc3)CCOCC2)c2cc(Cl)nc(N)n2)c1C]

6-chloro-4-N-{[4-(4-fluorophenyl)oxan-4-yl]methyl}-4-N-[(4-methoxy-3,5-dimethylpyridin-2-yl)methyl]pyrimidine-2,4-diamine was synthesized following the procedure described in EXAMPLE 1 and appropriate starting materials. Compound was produced as white solid (75 mg, 31% yield). $^1$H NMR (499 MHz, Chloroform-d) δ 8.06 (s, 1H), 7.34-7.19 (m, 2H), 7.04 (t, J=8.6 Hz, 2H), 5.55 (s, 1H), 4.70 (s, 2H), 3.91 (d, J=9.5 Hz, 2H), 3.71 (s, 3H), 3.55 (d, J=8.8 Hz, 2H), 2.18 (s, 3H), 2.16-2.00 (m, 2H), 1.88 (s, 3H), 1.58 (s, 2H); MS: m/z [M+H]$^+$ calculated for $C_{25}H_{29}ClFN_5O_2$, 487; found 487.

Example 3: 6-chloro-4-N-{[4-(4-fluorophenyl)oxan-4-yl]methyl}-4-N-[(4-methoxy-3-methylpyridin-2-yl)methyl]pyrimidine-2,4-diamine (Compound C)

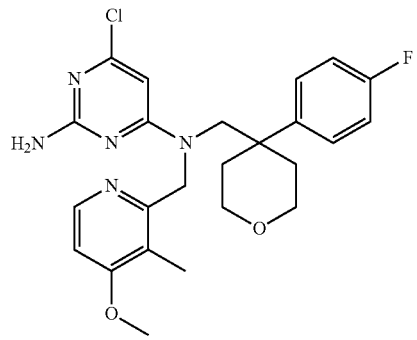 [SMILES: COc1ccnc(CN(CC2(c3ccc(F)cc3)CCOCC2)c2cc(Cl)nc(N)n2)c1C]

6-chloro-4-N-{[4-(4-fluorophenyl)oxan-4-yl]methyl}-4-N-[(4-methoxy-3-methylpyridin-2-yl)methyl]pyrimidine-2,4-diamine was synthesized following the procedure described in EXAMPLE 1 and appropriate starting materials. The resulting compound was produced as a white solid (155 mg, 66% yield). ¹H NMR (499 MHz, DMSO-d6) δ 8.10 (d, J=5.7 Hz, 1H), 7.53-7.31 (s, 2H), 7.27-7.05 (m, 2H), 6.83 (d, J=5.7 Hz, 1H), 6.35 (s, 2H), 5.71 (s, 1H), 3.79 (s, 3H), 3.30 (m, 2H) 2.69 (s, 7H), 2.18 (t, J=8.1 Hz, 5H), 1.95-1.85 (m, 4H); MS: m/z [M+H]⁺ calculated for $C_{24}H_{27}ClFN_5O_2$, 473; found 473.

Example 4: 6-chloro-4-N-[(4-methoxy-3,5-dimethylpyridin-2-yl)methyl]-4-N-{[4-(6-methylpyridin-2-yl)oxan-4-yl]methyl}pyrimidine-2,4-diamine (Compound D)

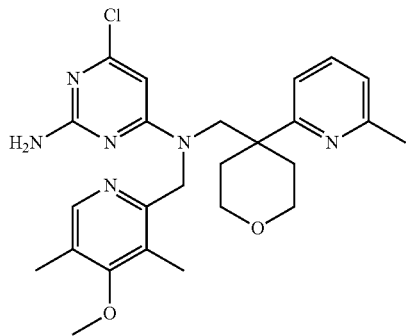 [SMILES: COc1c(C)cnc(CN(CC2(c3cccc(C)n3)CCOCC2)c2cc(Cl)nc(N)n2)c1C]

6-chloro-4-N-[(4-methoxy-3,5-dimethylpyridin-2-yl)methyl]-4-N-{[4-(6-methylpyridin-2-yl)oxan-4-yl]methyl}pyrimidine-2,4-diamine was synthesized following the procedure described in EXAMPLE 1 and appropriate starting materials. Compound was produced as a white solid (153 mg, 63% yield). ¹H NMR (499 MHz, DMSO-d₆) δ 8.02 (s, 1H), 7.60 (t, J=7.7 Hz, 1H), 7.20 (d, J=8.0 Hz, 1H), 7.11 (d, J=7.6 Hz, 1H), 6.29 (s, 2H), 5.61 (s, 1H), 3.76 (s, 4H), 3.67 (s, 3H), 3.26 (s, 4H), 2.49 (s, 3H), 2.43 (s, 3H), 2.12 (s, 3H), 1.85 (d, J=39.6 Hz, 4H); MS: m/z [M+H]⁺ calculated for $C_{25}H_{31}ClN_6O_2$, 484; found 484.

Example 5: 6-chloro-4-N-[(4-methoxy-3,5-dimethylpyridin-2-yl)methyl]-4-N-{[4-(pyridin-2-yl)oxan-4-yl]methyl}pyrimidine-2,4-diamine (Compound E)

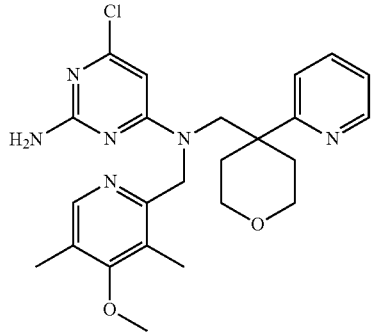 [SMILES: COc1c(C)cnc(CN(CC2(c3ccccn3)CCOCC2)c2cc(Cl)nc(N)n2)c1C]

6-chloro-4-N-[(4-methoxy-3,5-dimethylpyridin-2-yl)methyl]-4-N-{[4-(pyridin-2-yl)oxan-4-yl]methyl}pyrimidine-2,4-diamine was synthesized following the procedure described in EXAMPLE 1 and appropriate starting materials. Compound was produced as a white solid (140 mg, 60% yield). ¹H NMR (499 MHz, DMSO-d6) δ 8.59 (dd, J=1.8, 4.9 Hz, 1H), 8.01 (s, 1H), 7.73 (td, J=1.9, 7.7 Hz, 1H), 7.45 (d, J=8.0 Hz, 1H), 7.27 (ddd, J=1.0, 4.7, 7.4 Hz, 1H), 6.29 (s, 3H), 5.63 (s, 1H), 3.77 (s, 4H), 3.66 (s, 3H), 3.30-3.09 (m, 4H), 2.31 (m, 3H), 2.12 (s, 3H), 1.97-1.75 (m, 4H); MS: m/z [M+H]⁺ calculated for $C_{24}H_{29}ClN_6O_2$, 470; found 470.

Example 6: 6-chloro-4-N-[(4-chloro-3,5-dimethylpyridin-2-yl)methyl]-4-N-{[4-(4-fluorophenyl)oxan-4-yl] methyl}pyrimidine-2,4-diamine (Compound B)

(a) 2-(chloromethyl)-3,5-dimethylpyridin-4-ol

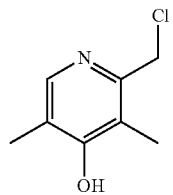

In a 50 mL round bottom flask, 3,5-dimethyl 4-methoxypyridine hydrochloride (444 mg, 2.0 mmol) was suspended in dichloromethane (5.0 mL). Then added boron tribromide (1.0 M in dichloromethane) solution (6.0 mL, 6.0 mmol) to the reaction mixture at 0° C. using syringe. Then slowly allowed to room temperature and continued overnight. Then cooled to 0° C. and quenched with sat.NaHCO₃ solution followed by 5.0 mL water. Then extracted with ethyl acetate (10 mL). Then aqueous layer basified with more sat-.NaHCO₃ solution and precipitated product collected by filtration. Dried the product (180 mg) and used in next step without further purificaiton. MS: m/z [M+H]⁺ calculated for $C_8H_{10}ClNO$, 172; found 172.

(b) 4-chloro-2-(chloromethyl)-3,5-dimethylpyridine hydrochloride

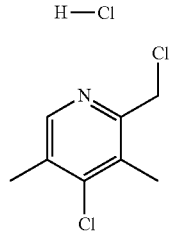

In a 10 mL glass vial, 2-(chloromethyl)-3,5-dimethylpyridin-4-ol (172 mg, 1.0 mmol) was suspended in POCl3 (2.0 mL), then closed the cap and heated at 80° C. for an hour. Then evaporated completely to dryness and analyzed to obtain tan solid (225 mg) used directly in next step. MS: m/z [M+H]⁺ calculated for $C_8H_9Cl_2N$, 191; found 191.

(c) [(4-chloro-3,5-dimethylpyridin-2-yl)methyl]({[4-(4-fluorophenyl)oxan-4-yl]methyl})amine

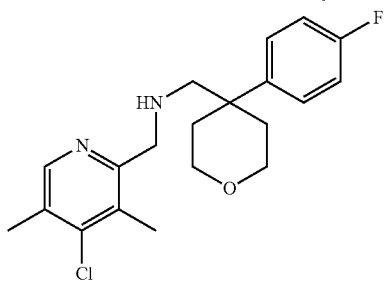

[(4-chloro-3,5-dimethylpyridin-2-yl)methyl]({[4-(4-fluorophenyl)oxan-4-yl]methyl})amine was synthesized following the procedure described in EXAMPLE 1 and appropriate starting materials. Compound was produced as gummy solid (251 mg). MS: m/z [M+H]$^+$ calculated for $C_{20}H_{24}ClFN_2O$, 364; found 364.

(d) 6-chloro-4-N-[(4-chloro-3,5-dimethylpyridin-2-yl)methyl]-4-N-{[4-(4-fluorophenyl)oxan-4-yl]methyl}pyrimidine-2,4-diamine (Compound B)

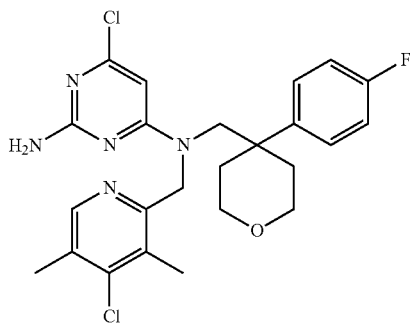 [SMILES: Cc1cnc(CN(CC2(c3ccc(F)cc3)CCOCC2)c2cc(Cl)nc(N)n2)c(C)c1Cl]

6-chloro-4-N-[(4-chloro-3,5-dimethylpyridin-2-yl)methyl]-4-N-{[4-(4-fluorophenyl)oxan-4-yl]methyl}pyrimidine-2,4-diamine was synthesized following the procedure described in EXAMPLE 1 and appropriate starting materials. Compound was produced as a white solid (38 mg, 16% yield). $^1$H NMR (499 MHz, DMSO-d$_6$) δ 8.14 (s, 1H), 7.41 (t, J=7.0 Hz, 2H), 7.15 (t, J=8.8 Hz, 2H), 6.38 (s, 2H), 5.69 (s, 1H), 3.83 (m, 4H), 2.23 (s, 3H), 1.97 (m, 8H); MS: m/z [M+H]$^+$ calculated for $C_{24}H_{26}Cl_2FN_5O$, 491; found 491.

Example 7: Preparation of Compound A

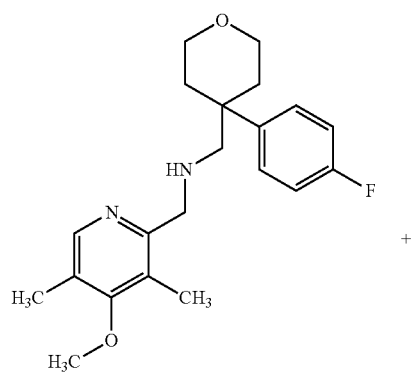

101

+

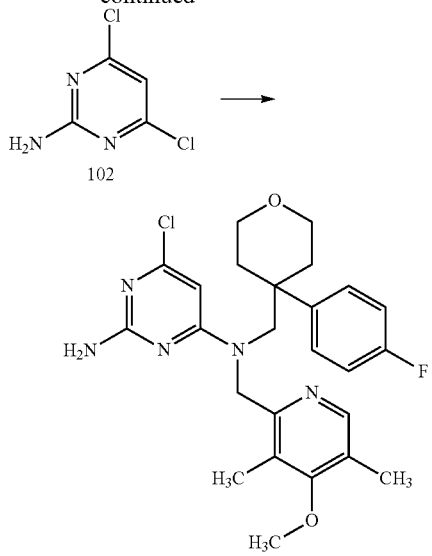

102

Method (a) In a 4.0 ml glass vial starting materials 101 and 102 were combined in 2 ml EtOH. The Et3N was added and reaction was continued at 100° C. for 3 hours. The product was transferred into round bottom flask (25 ml) and 5 ml of CH2Cl2 was added and evaporated under reduced pressure. Following which an additional 30 ml of CH2Cl2 was added and washed with water in a separatory funnel. The separated organic layer was dried on sodium sulfate and evaporated. The residue was purified on VCC using hexane-EtOAc (0-100%) and pure product fractions combined and evaporated to the final product CAP01088. The yield of the final product was 75 mgs and confirmed by NMR and mass spectra. $^1$H NMR (499 MHz, CDCl3): δ 8.06 (s, 1H), 7.34-7.19 (m, 4H), 7.04 (t, j=8.6 Hz, 2H), 5.55 (s, 1H), 4.70 (s, 2H), 3.91 (d, J=9.5 Hz, 2H), 3.71 (s, 3H), 3.55 (d, J=8.8 Hz), 2.18 (s, 3H), 2.16-2.00 (m, 3H), 1.88 (s, 3H), 1.58 (s, 2H). Calculated Mass: 486; found 486.9.

Method (b) 2-(Chloromethyl)-4-methoxy-3,5-dimethyl pyridine hydrochloride (101) was dissolved in DMF and treated with the corresponding nucleophile primary amine (102), followed by N,N-Diisopropylethylamine (DIPEA). The resulting reaction mixture was heated using microwave irradiation at 120° C. for 10 min. Upon completion of the reaction, the crude disubstituted amine (3) products were purified using automated preparative HPLC. The suspension of the amine product from the above reaction and 4-R, 6-chloro-pyrimidine-2-amine (4) were then dissolved in DMF and treated with Et3N and the resulting reaction mixture was heated at 65° C. for 2.5 hours. After aqueous workup, the crude products were purified using automated preparative HPLC to yield the final pyrimidine analogues as desired product.

BIOLOGICAL ASSAYS

General Methods

Recombinant Proteins

Recombinant full-length human Hsp90 and 459 TRAP1 were cloned into a pET vector for *E. coli* expression engineered with a TEV-cleavable N-terminal 6His-affinity purification tag. Prior to transforming into BL21 (DE3) all the cloned vectors were sequence confirmed. Expressed proteins were purified using NTA resin (Life Technologies) followed by size exclusion chromatography using FPLC. The molecular mass of the purified proteins was confirmed by MALDI-TOF and assessed for purity by SDS-PAGE.

Cell Culture

U251MG cells were maintained at 37° C. and 5% $CO_2$ in RPMI media supplemented with glutamax and containing 10% heat-inactivated fetal bovine serum and 1% penicillin/streptomycin (Life Sciences).

Fluorescence Polarization (FP) Displacement Assay

FP assays are based on quantitating displacement of Hsp90 or TRAP1 inhibitor for FITC-labeled geldanamycin (GA-FITC) and was performed as described by Howes R, Barril X, Dymock B W, Grant K, Northfield C J, et al. (2006) A fluorescence polarization assay for inhibitors of Hsp90 (2006). Anal Biochem. 350:202-213. The assay conditions were 20 mM HEPES, pH-7.5, 50 mM KCl, 5 mM $MgCl_2$, 20 mM sodium molybdate, 2 mM DTT, 0.01% NP40, 100 ug/ml BSA, 50 nM Hsp90 or 200 nM TRAP1, 1% DMSO, and 8 nM (for Hsp90) or 20 nM (for TRAP1) GA-FITC in the presence of increasing concentrations of test compound. Assay mixtures were incubated at 4° C. for 24 h and changes in FP in the wells were measured at ambient temperature with a POLARstar Omega micro-titer plate reader at an excitation of 485 nm and emission of 520 nm.

Cell Viability Assay

A cell counting kit (CCK-8 assay kit, Dojindo) and an ADP-Glo assay (Life Technologies) were used to quantitate the effects of test compounds on cell viability. U251MG cells were seeded into 96 well tissue culture plates and incubated for 16 h at 37° C. with 5% CO2. Increasing concentrations of test compounds were added to the wells from DMSO-containing stock solutions to a final DMSO concentration of 0.05% and incubated for 72 hr at 37° C. CCK-8 kit reagent or ADP-GLO reagent were then added to the wells and absorbance was measured at 450 nm (for the CCK assay) using a Synergy HT micro-titer plate reader (Biotek) or luminescence was measured (for the ADP-GLO assay) using a POLARstar Omega micro-titer plate reader (BMG).

Caspase Activation Assay

U251MG cells were seeded, maintained, and treated with test compounds as described above for 48 h at 37° C. Quantification of total cellular Caspase-3 and 7 activity was accomplished using a Caspase-3/7 luminescence assay kit (Promega) according to the manufacturer's recommendations and analyzed with a POLARstar Omega micro-titer plate reader (BMG).

Biomarker Quantitation

U251 cells were plated in 6 well format culture dishes overnight at 37° C. with 5% CO2 and then treated with increasing concentrations of test compounds for 48 h at 37° C. with 5% CO2. Quantification of total Akt1, EGFR, and Hsp70 in cell lysates was accomplished using ELISA kits (R&D Systems) according to the manufacturer's recommendations and utilizing a Synergy HT micro-titer plate reader (Biotek). Cell lysates were prepared as recommended in the kit procedure. Protein concentrations of lysates clarified using centrifugation were determined using a Bradford assay (Thermo Scientific), and the values were used to normalize the biomarker values.

Tetramethylrhodamine Ethyl Ester (TMRE) Assay

For cell-based assays, cells were treated with various concentrations of the test compounds for 48 hours at 37° C., with 5% $CO_2$. TMRE (200 nM) was then added to wells for 30 min and monitored for changes in fluorescence activity either by fluorescence microscopy using an inverted Zeiss LSM 710 confocal microscope or by spectrophotometry using a fluorescence plate reader ($544_{ex}/590_{em}$) after washing the cells. Specific TMRE fluorescence was calculated by comparison to matched wells pretreated with 20 uM FCCP for 10 min prior to addition of TMRE. For mitochondria assays, untreated U251MG cells grown to confluence in T75 culture flasks. Mitochondria from these cells were isolated using a mitochondria isolation kit (Thermo Scientific) and loaded with 0.1 mM TMRE in kit buffer at 37° C. for 20 min. After washing, the TMRE-loaded mitochondria (2 ug per well) were incubated in a 96 well black plate with test compounds and monitored kinetically at 30° C. for changes in fluorescence using a fluorescence plate reader (ex 544/em 590). The fluorescence intensity after treatment with 20 um FCCP in control wells corresponded to a fully depolarized state.

Mitochondrial Respiratory Function Assay

The effect of test compounds on the mitochondrial oxygen consumption rate (OCR) was determined in real time using a Seahorse Xr24 extracellular flux analyzer (Seahorse Bioscience). The cell-based assay was performed essentially as recommended by the manufacturer. Briefly, cells were seeded in a 24 well XF plate using an appropriate cell density. "Flux Pak" cartridge (containing the $O_2$ and $H^+$ sensitive fluorophores) were hydrated in the XF calibrant solution overnight just prior to running the assay. On the following day, the cells were replenished with XF assay media (unbuffered DMEM containing 10 mM glucose and 2 mM pyruvate) and placed in a $CO_2$ free 37° C. incubator for an additional one hour. Basal OCR was measured before the wells were injected with test compounds. Subsequently, mitochondrial bioenergetics stress was determined by treating the cells sequentially with 0.125 mg/ml Oligomycin (ATP synthase inhibitor), 0.5 mM FCCP (uncoupler) and 1 mM rotenone (Complex I inhibitor) while continuously measuring the OCR.

Figure 1:
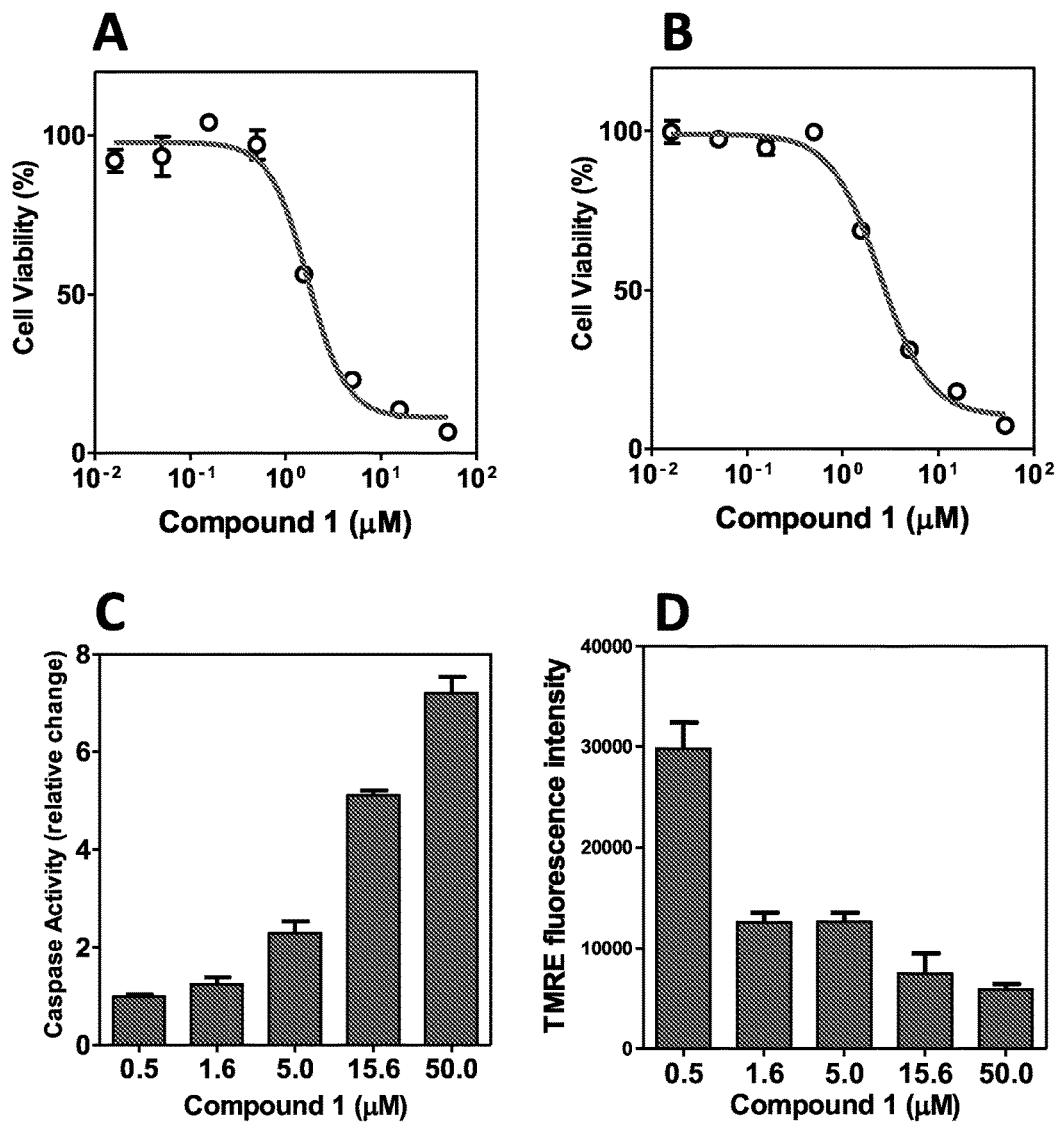
FIG. 1 represents cell viability where (A) represents U251MG cell viability in the presence of Compound 1 measuring cellular dehydrogenase activity; (B) represents U251MG cell viability in the presence of Compound 1 measuring ATP quantitation; (C) represents U251MG caspase 3/7 activity in the presence of Compound 1; and (D) represents TMRE fluorescence in U251MG cells after treatment with Compound 1.

Potency and U251MG Cellular Efficacy of Hsp90/TRAP1 Inhibitors of Formula (I):

The Hsp90i Ki value for Compound 1 was determined to be 39.4 nM and the TRAP1 Ki value was determined to be 50.4 nM. Compound 1 was then evaluated for Hsp90 inhibitor efficacy in a variety of U251MG cell-based assays. U251MG cell viability in the presence of Compound 1 after incubation with cells for 72 h at 37° C. was determined using cellular dehydrogenase activity and ATP quantitation. Both assays gave similar results with Compound 1 yielding $IC_{50}$ values of 1.72 and 2.5 uM (FIGS. 1A and 1B). U251MG caspase 3/7 activity increased 6.8 fold after 48 h in the presence of 50 uM Compound 1 (FIG. 1C). An increase in caspase activity was observed in the presence of a concentration as low as 1.6 uM for Compound 1. The increase in caspase 3/7 activity, a measure of apoptosis, was directly proportional to the failure of cells to sequester TMRE, the latter reflective of a mitochondrial permeability transition, in cells after a 48 hr treatment with Compound 1 (FIG. 1D).

Figure 2:
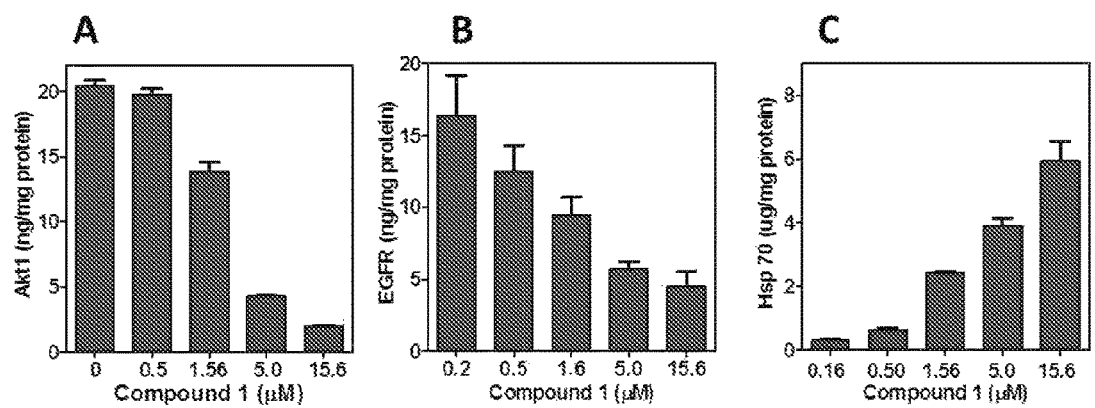
FIG. 2 represents cell client protein degradation and Hsp70 induction where (A) represents reduced Akt1 levels upon treatment with Compound 1; (B) represents a reduction in EGFR levels upon treatment with Compound 1; (C) represents an increase in Hsp70 levels upon treatment with Compound 1.

Increased Akt activation and EGFR expression are hallmarks in GMB. ELISA was used to quantify Hsp90 inhibitor-mediated degradation of Akt1 and EGFR. Compound 1 significantly reduced Akt1 levels with a reduction of 79% at a concentration of 15.6 uM, with an $IC_{50}$ value of 2.4 uM (FIG. 2A). EGFR levels were reduced by 71% at a concentration of 16 uM for Compound 1 (FIG. 2B). Hsp70 is a well-established biomarker for Hsp90 inhibitors that characteristically increases in cells in response to Hsp90 inhibition. Hsp70 levels in U251MG cells increased 6-fold in the presence of 15.6 uM Compound 1 at a same concentration (FIG. 2C).

Mitochondrial Targeting of Hsp90/TRAP1 Inhibitors:

TRAP1 is regarded as an important molecular target for cancer therapy by virtue of its key role in preserving mitochondrial integrity under conditions of cellular stress. TRAP1 inhibitors have been shown to induce cancer cell apoptosis by causing a rapid mitochondrial permeability transition, and may also participate in pro-survival pathways responsible for multi-drug resistance. To determine if the apoptotic effects of the compounds described herein on U251MG cells exhibited a similar pattern on mitochondrial integrity, cells were treated with Compound 1 under same the conditions used in the caspase assay, after which the cells were then treated with TMRE for 30 min, with or without prior treatment with FCCP. The results showed a decrease in specific TMRE fluorescence indicative of a decrease in mitochondrial membrane potential that was proportional to the concentration of Compound 1 (FIG. 1D) and paralleled the increase in caspase 3/7 activity (FIG. 1C). Specific TMRE fluorescence decreased by 42% at 5 uM for Compound 1 vs untreated and by 73% at 50 uM for Compound 1.

Figure 3:
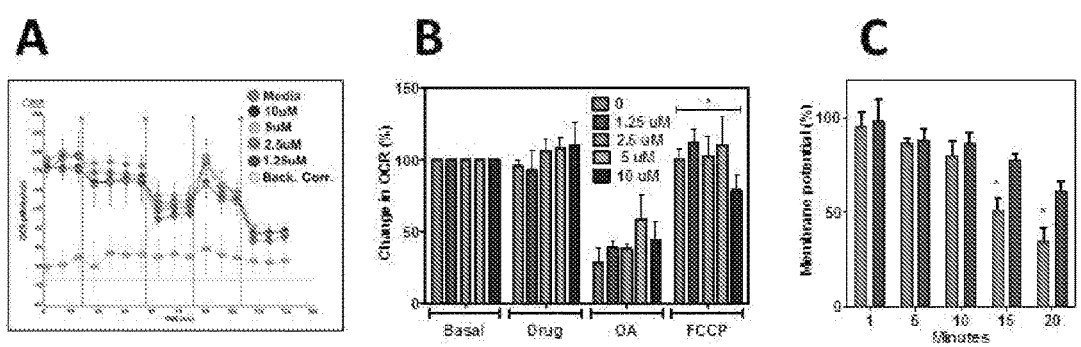
FIG. 3 represents mitochondrial integrity where (A) represents mitochondrial OCR before and after treatment with Compound 1; (B) represents oxidative stress upon treatment with Compound 1; (C) represents TMRE-loaded mitochondria isolated from U251MG cells treated with Compound 1.

The effect of compounds on U251MG cell mitochondrial function was also assessed by measuring the mitochondrial respiration rate under stressed conditions by incubating cells in the presence of Compound 1 after sequential addition of the mitochondrial stressors oligomycin, FCCP, and rotenone. Compound 1 caused a rapid (minutes) dose-dependent decrease in the ORC, indicative of dysfunctional mitochondrial bioenergetics and increased oxidative stress (FIGS. 3A and 3B). To verify that Compound 1 was gaining access to TRAP1 and Hsp90 located in the mitochondrial matrix, Compound 1 was incubated at 30° C. with TMRE-loaded mitochondria isolated from U251MG cells and continually monitored for changes in TMRE fluorescence intensity. Compound 1 caused a dose-dependent decrease in mitochondrial potential (FIG. 3C) within minutes suggesting that the compounds effectively penetrated the mitochondrial outer and inner membranes and are capable of directly disrupting the functional integrity of isolated mitochondria via TRAP1 and mitochondrial Hsp90 inhibition. Compound 1 reduced membrane potential to 52% (20 uM) and 61% (4 uM).

Programmed Tumor Cell Death and Cellular Biomarker Assays

Figure 4:
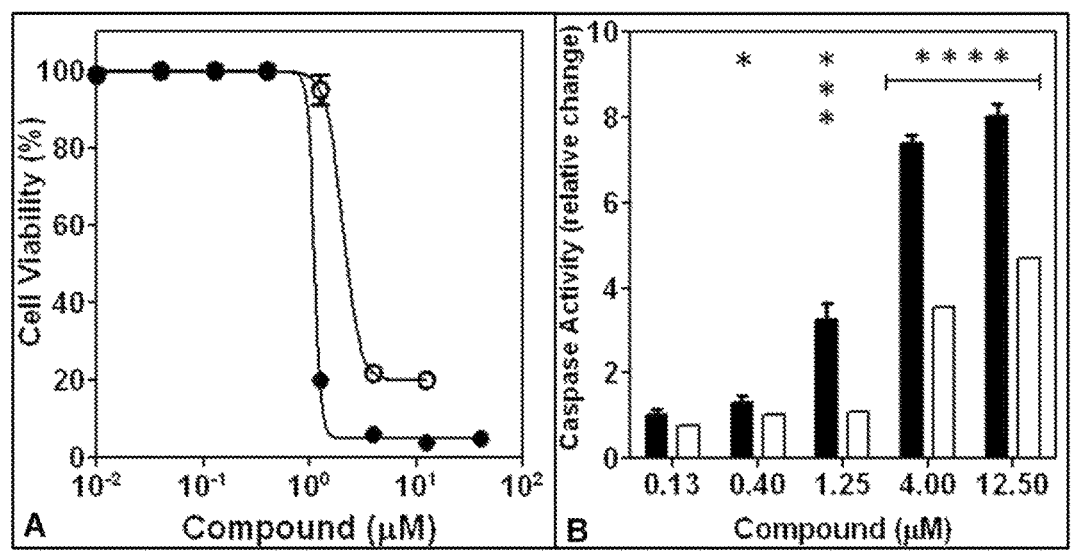
FIG. 4 is a graphical depiction where A. plots the cellular efficacy ($EC_{50}$, μM) of Compound A (filled circle) and Compound B (open circle) in the MDA-MB-231 breast cancer cell line. Cell viability was determined using the CellTiter-Glo assay (Promega), following the manufacturer's protocol; and B. plots the effects of Compound A and Compound B on caspase activity in MDA-MB-231 cell line. Caspase 3/7 activity was measured after treatment with Compound A (solid bar) or Compound B (open bar) for 48 hours using a Caspase Glo 3/7 assay kit (Promega). Statistical significance was determined using a one-tailed student's t test. . p>0.01, *, p<0.001; ****, p<0.0001.

Programmed Cell Death:

Tumor cell lines MDA-MB-23 1and HEI-193 were obtained from ATCC and the UCSD Veterans Medical Center, respectively. Cells were cultured in culture medium and passaged after lifting using 0.25% trypsin/EDTA. Cells were seeded into a 96 well tissue culture plate at $1.3 \times 10^4$ cells per well in a volume of 100 µL of culture medium. After the cells were cultured for 24 hours, increasing concentrations of Hsp90 inhibitor were added to wells in triplicate from DMSO containing stock solutions and mixed by gently by stirring. Final DMSO concentration in all wells was 0.25%. The cells were cultured for 48 hours. Caspase 3/7 activity was measured using a Homogeneous Caspase 3/7 Assay Kit used according to the manufacturer's recommendations. In detail, an equal volume of Caspase 3/7 Assay Kit reagent was added to the wells and fluorescence readings (Ex/Em 485/528) were taken after 3, 6, and 23 hours at ambient temperature using a micro-titer plate reader. A rhodamine 110 stock solution (10 mM) was prepared in DMSO and diluted with water within a range from 4000-62.5 nM. Fluorescence intensities of the dilutions were measured to obtain a standard curve. Cells were seeded into tissue culture plates using culture medium. After seeding, cultures were incubated for 16 hours at 37° C. with 5% $CO_2$. Increasing concentrations of Hsp90 inhibitor were added to the culture from DMSO containing stock solutions and mixed gently by stirring. Final DMSO concentration in all wells was 0.25%. Cultures were plated in 386 well format and incubated for 72 hours at 37° C. with 5% $CO_2$. Cell viability was measured with the ATPlite Kit (Perkin Elmer) used according to the manufacturer's recommendation. Cultures were equilibrated at ambient temperature for 30 min and 10 µl of ATPlite Kit reagent was added to each well. Cultures were mixed at 1,000 rpm for 2 min in the dark and luminescence quantification was accomplished using a micro-titer plate reader (POLARstar Omega micro-titer plate reader; BMG Labtech) (FIGS. 4 and 7).

Cellular biomarker assays: Cells were cultured in culture medium (RPMI-glutamax, 10% FCS, 100 units/ml penicillin, and 100 µg/ml streptomycin). Cells were passaged after lifting using 0.25% trypsin/EDTA, and $3 \times 10^5$ cells were seeded in each well of six well plates (total volume 2.5 mL/well). After the cells were cultured for 24 hours, increasing concentrations of Hsp90 inhibitor were added to wells in triplicate from DMSO-containing stock solutions and mixed by gently by stirring. Final DMSO concentration in all wells was 0.25%. The treated cells were then cultured for 48 hours prior to lysate preparation. The culture media was removed from wells, and the wells were washed twice with DPBS containing 1 mM $CaCl_2$ and 0.5 mM $MgCl_2$. Cells were then lysed in lysis buffer (PBS, 0.5% TX-100, 1 mM EDTA, 5 mM NaF, 1 mM sodium orthovanadate, 2.5 mM sodium pyrophosphate, and 1×HALT protease inhibitor.) One hundred µL of lysis buffer per well was used for 6 well plates and 40 was used for 12 well plates. Lysates were stored at −80° C. until assayed for Akt1 and ERK1. The protein concentration in the cell lysates was determined using the BCA protein assay kit used according to the manufacturer's recommendations. Twenty five µL of a 1:10 dilution of each lysate in PBS were added to wells of a 96 well plate. A standard curve was prepared by adding 25 µL of bovine serum albumin protein (provided with the BCA protein assay kit) dilutions ranging from 2.0-0.125 mg/ml. Two hundred µL of BCA Protein Assay Kit reagent was added and the mixtures were incubated at 37° C. for 30 min. Protein concentrations were determined using a micro-titer plate reader (Model # Synergy HT; BioTek Inc., Winooski, Vt.).

Figure 5:
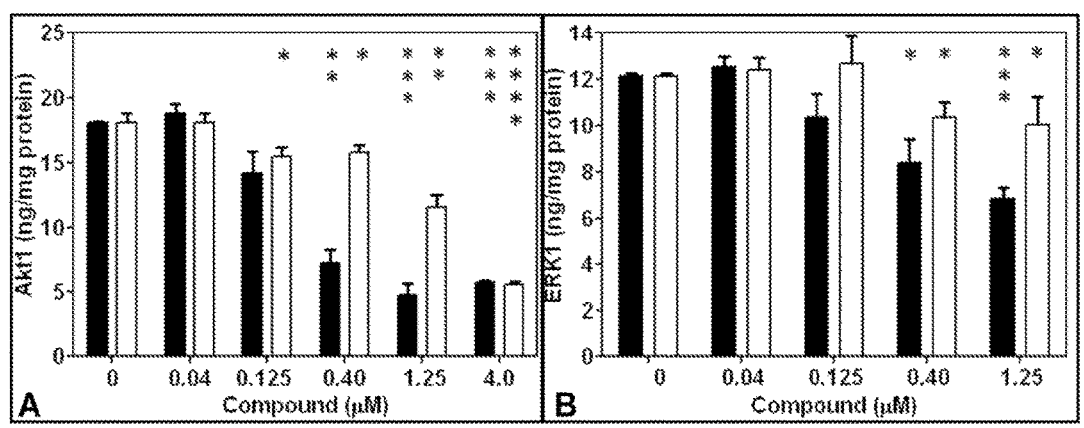
FIG. 5 is a graphical depiction showing the in vitro PD effects of Compound A and Compound B showing suppression of Hsp90 client proteins in MDA-MB-231 cell line. Akt1 (A) and ERK1 (B) levels were quantitated in cell lysates after treatment with Compound A (solid bar) or Compound B (open bar) for 48 hours using ELISA kits from R&D Systems. Statistical significance was determined as in FIG. 4

Akt1 and ERK1 levels in the cell lysates were measured using kits from R&D Systems used according to the manufacturer's recommendations. Cell lysates were assayed at a 1:24 dilution for the Akt1 and ERK1 ELISA. The Akt1 and ERK1 concentrations in the cell lysates were extrapolated from the standard curve and corrected for lysate protein concentration. Akt1 and ERK1 levels were determined using a micro-titer plate reader (Model # Synergy HT; BioTek Inc., Winooski, Vt.) (FIGS. 5 and 8).

Cellular Biomarker Assays Using Mayo Clinic Patient Derived (PDX) GBM Cell Lines:

Short-term explant cultures from PDX models were seeded into 96-well Perfecta3D hanging drop plates to form a single spheroid in each well after 2 days. The spheroids were transferred to a round bottom 96 well plate by centrifugation and then incubated with graded concentrations of test compound (8 spheroids per compound concentration). Spheroid volumes were monitored every 6 hours over the course of 5 days using the IncuCyte system (Essen BioScience, MI, US) to provide a growth curve akin to a tumor regrowth assay. In vitro pharmacodynamic effects of CAP01088 and CAP01100 showing suppression of Hsp90 client proteins (EGFR and Akt1) in clinically relevant Mayo Clinic GBM PDX cell lines were quantitated in cell lysates from three Mayo Clinic GBM PDX cells lines after treatment with no drug (first bar) or CAP01088 or CAP01011 for 48 hours using ELISA kits from R&D Systems (FIGS. 10 and 11).

Mitochondrial Uptake and Membrane Potential Depolarization

Figure 6:
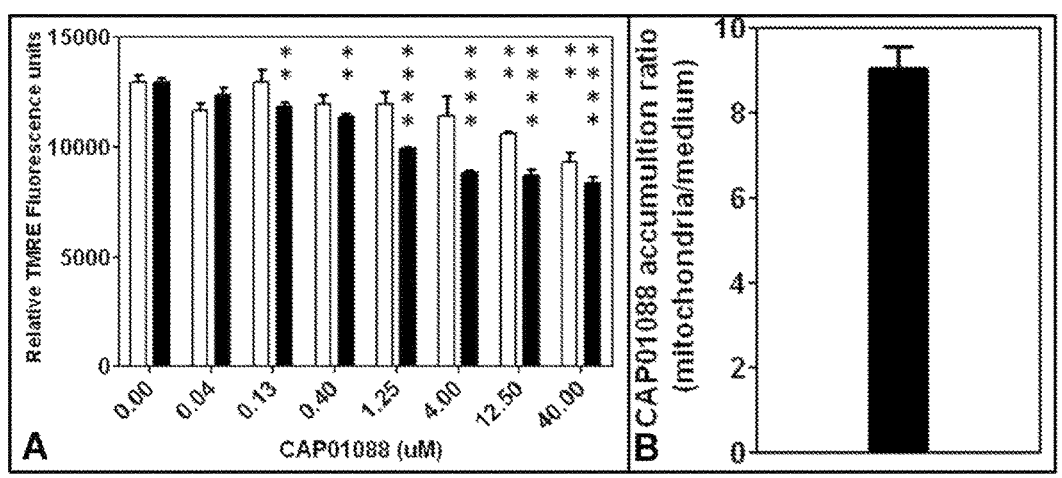
FIG. 6 is a graphical depiction showing the effects of Hsp90/TRAP1 inhibitor on MDA-MB-231 cell mitochondrial integrity. (A) Compound A causes a dose-dependent decrease in Tetramethylrhodamine, ethyl ester (TMRE) fluorescence of MDA-MB-231 cells indicative of mitochondrial dysfunction, 2 hours (open bar) or 4 hours (solid bar). (B) Quantitation of Compound B accumulation in mitochondria isolated from MDA-MB-231 cell compared with the level in the culture medium. Data are mean±SEM of triplicate samples from two independent experiments.

Mitochondrial integrity was evaluated using Tetramethylrhodamine ethyl ester (TMRE) assay. A TMRE assay kit (Abcam) was used to evaluate Hsp90/TRAP1 inhibitor-induced changes in mitochondrial membrane potential. For whole cell assays, cells were treated with various concentrations of the test compounds for 48 hours at 37° C., with 5% $CO_2$. TMRE (200 nM) was then added to wells for 30 min and monitored for changes in fluorescence activity using a fluorescence plate reader (ex544/em 590) after washing the cells. Specific TMRE fluorescence was calculated by comparison to matched wells pretreated with the depolarizing proton ionophore carbonyl cyanide 4-(trifluoromethoxy)phenylhydrazone (FCCP) at 20 uM 10 min prior to addition of TMRE. For mitochondria assays, mitochondria was isolated using a kit from Thermoscientific and loaded with 0.1 mM TMRE. TMRE-loaded mitochondria (2 μg per well) were incubated with test compounds and monitored kinetically at 30° C. for changes in fluorescence using a flurorescence plate reader (ex 544/em 590) (FIGS. 6A, 9A and 12).

Analysis of Drug Accumulation in the Mitochondria

Mitochondria (100 μg) isolated from MDA-MB-231 and HEI-194 tumor cell lines were incubated with 20 μM CAP01088 for 30 mins at 30° C. in mitochondrial incubation buffer (MIB: 0.2M sucrose, 10 mM Tris-MOPS, pH 7.4, 5 mM succinaye, 1 mM Pi, 2 μM rotenone, and 10 μM EGTA with modifications as needed). The mitochondria were chilled on ice and collected by centrifugation at 8000 g for 10 min. The supernatant was collected and the mitochondrial pellet was washed twice with MIB and dissolved in lysis buffer (acetonitrile/methanol, 3:1). The concentration of CAP01088 in supernatant and mitochondrial extract was analyzed using a Waters HPLC/Mass spectrometer (FIGS. 6B and 9B).

The results are also tabulated herein below:

TABLE 1

Preliminary SAR of compounds designed and synthesized based on proposed medicinal chemistry plan

| Compd ID | Mol. Str. | Mol. Wt. (Da) | cLog P | PSA ($A^2$) | HSP90 Ki | HSP90 $IC_{50}$ | TRAP1 Ki | TRAP1 $IC_{50}$ |
|---|---|---|---|---|---|---|---|---|
| C | [structure] | 472.0 | 4.28 | 86.4 | 22 | 87 | NA | >4000 |
| D | [structure] | 483.0 | 3.43 | 99.3 | 14 | 54 | 68 | 543 |

TABLE 1-continued

Preliminary SAR of compounds designed and synthesized based on proposed medicinal chemistry plan

| Compd ID | Mol. Str. | Mol. Wt. (Da) | cLog P | PSA ($A^2$) | Biochemical efficacy (nM) | | | |
|---|---|---|---|---|---|---|---|---|
| | | | | | HSP90 | | TRAP1 | |
| | | | | | Ki | $IC_{50}$ | Ki | $IC_{50}$ |
| E | [structure] | 468.9 | 3.37 | 99.3 | 24 | 96 | 138 | 1100 |

NA: Not active; ND: Not determined

TABLE 2

Molecular and biochemical potency of CAP01088, CAP1100 & Ganetespib

| Compd ID | Mol. str. | Mol. Wt. | cLog P | PSA ($A^2$) | Biochemical efficacy (nM) | | | |
|---|---|---|---|---|---|---|---|---|
| | | | | | HSP90 | | TRAP1 | |
| | | | | | Ki | $IC_{50}$ | Ki | $IC_{50}$ |
| A | [structure] | 486.0 | 4.71 | 86.4 | 11 | 44 | 39 | 312 |
| B | [structure] | 490.4 | 5.33 | 77.20 | 8 | 33 | 11 | 85 |

TABLE 2-continued

Molecular and biochemical potency of CAP01088, CAP1100 & Ganetespib

| Compd ID | Mol. str. | Mol. Wt. | cLog P | PSA ($A^2$) | Biochemical efficacy (nM) | | | |
|---|---|---|---|---|---|---|---|---|
| | | | | | HSP90 | | TRAP1 | |
| | | | | | Ki | IC$_{50}$ | Ki | IC$_{50}$ |
| Ganetespib | 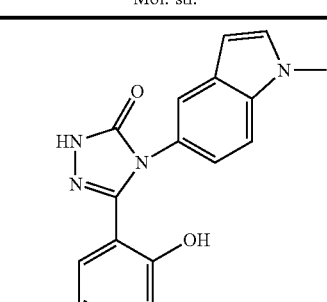 | 364.40 | 3.64 | 96.1 | 4.8 | 20 | 11.5 | 89 |

TABLE 3

Cellular efficacy [EC$_{50}$ (µM)] of dual-acting HSP90/TRAP1 inhibitors in clinical relevant Mayo Clinic GBM PDX cell lines

| Compd. ID | Cell line | | |
|---|---|---|---|
| | GBM10 | GBM39 | GBM43 |
| A | 0.28 | 0.22 | 0.28 |
| B | 1.20 | 0.62 | 0.87 |

The above preferred embodiments and examples were given to illustrate the scope and spirit of the present invention. These embodiments and examples will make apparent to those skilled in the art other embodiments and examples. The other embodiments and examples are within the contemplation of the present invention. Therefore, the present invention should be limited only by the appended claims.

What is claimed is:

1. A compound of Formula (I):

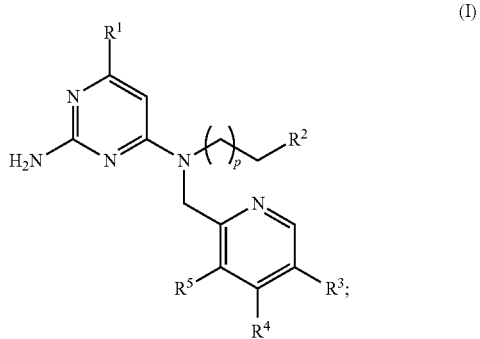

(I)

or a pharmaceutically acceptable salt thereof, wherein
R$^1$ is hydrogen, halo, (C$_1$-C$_3$)alkyl, halo(C$_1$-C$_3$)alkyl, (C$_1$-C$_3$)alkoxy, or halo(C$_1$-C$_3$)alkoxy;
R$^3$, R$^4$, and R$^5$ are independently hydrogen, halo, (C$_1$-C$_3$)alkyl, halo (C$_1$-C$_3$)alkyl, (C$_1$-C$_3$)alkoxy, halo(C$_1$-C$_3$)alkoxy, cyano,

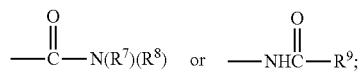

R$^2$ is heteroaryl or heterocycyl, each of which are optionally substituted with 1 to 2 groups independently selected from R$^6$, but not 4-morpholinyl or benzo[d][1,3]dioxol-5-yl;
p is 0, 1, or 2;
R$^6$ is selected from halo, cyano, nitro, amino, hydroxy, carboxy, (C$_1$-C$_6$)alkyl, heterocyclyl, aryl, arylalkyl, heteroaryl, heteroalkyl, heterocyclylalkyl, hydroxy(C$_1$-C$_6$)alkyl, CO$_2$H, (CH$_2$)$_{1-3}$COOH, (C$_1$-C$_3$)alkylcarbonyloxy, (C$_3$-C$_6$)cycloalkyl, hydroxy(C$_3$-C$_6$)cycloalkyl, (C$_4$-C$_7$)cycloalkylalkyl, (C$_2$-C$_6$)alkenyl, halo(C$_2$-C$_6$)alkenyl, hydroxy(C$_2$-C$_6$)alkenyl, (C$_2$-C$_6$)alkynyl, (C$_3$-C$_6$)cycloalkyl(C$_2$-C$_4$)alkynyl, halo(C$_1$-C$_6$)alkyl, halo (C$_3$-C$_6$)cycloalkyl, halo(C$_4$-C$_7$)cycloalkylalkyl, (C$_1$-C$_6$)alkoxy, (C$_3$-C$_6$)cycloalkoxy, (C$_4$-C$_7$)cycloalkylalkoxy, halo(C$_1$-C$_6$)alkoxy, halo(C$_3$-C$_6$)cycloalkoxy, halo(C$_4$-C$_7$)cycloalkylalkoxy, (C$_1$-C$_6$)alkylthio, (C$_3$-C$_6$)cycloalkythio, (C$_4$-C$_7$)cycloalkylalkylthio, halo(C$_1$-C$_6$)alkylthio, halo(C$_3$-C$_6$)cycloalkythio, halo(C$_4$-C$_7$)cycloalkylalkylthio, (C$_1$-C$_6$)alkylsulfinyl, (C$_3$-C$_6$)cycloalkylsulfinyl, (C$_4$-C$_7$)cycloalkylalkylsulfinyl, halo(C$_1$-C$_6$)alkylsulfonyl, halo (C$_3$-C$_6$)cycloalkylsulfinyl, halo(C$_4$-C$_7$)cycloalkylalkylsulfinyl, (C$_1$-C$_6$)alkylsulfonyl, (C$_3$-C$_6$)cycloalkylsulfonyl, (C$_4$-C$_7$)cycloalkylalkylsulfonyl, halo(C$_3$-C$_6$)cycloalkylsulfonyl, halo(C$_4$-C$_7$)cycloalkylalkylsulfonyl, (C$_1$-C$_6$)alkylamino, di(C$_1$-C$_6$)alkylamino, (C$_1$-C$_6$)alkoxy(C$_1$-C$_6$)alkoxy, halo(C$_1$-C$_6$)alkoxy(C$_1$-C$_6$)alkoxy, (C$_1$-C$_6$)alkoxycarbonyl, H$_2$NCO, H$_2$NSO$_2$, (C$_1$-C$_6$)alkylaminocarbonyl, di(C$_1$-C$_6$)alkylaminocarbonyl, (C$_1$-C$_3$)alkoxy(C$_1$-C$_3$)alkylaminocarbonyl, heterocyclylcarbonyl, (C$_1$-C$_6$)alkylaminosulfonyl, di(C$_1$-C$_6$)alkylaminosulfonyl, heterocyclylsulfonyl, (C$_1$-C$_6$)alkylcarbonylamino, (C$_1$-C$_6$)alkyl-carbonylamino(C$_1$-C$_6$)alkyl, (C$_1$-C$_6$)alkylsulfonylamino, (C$_1$-C$_6$)alkylsulfonylamino(C$_1$-C$_6$)alkyl, (C$_1$-C$_6$)alkoxycarbonyl(C$_1$-C$_6$)alkoxy, (C$_1$-C$_6$)alkoxy (C$_1$-C$_6$)alkyl, halo(C$_1$-C$_6$)alkoxy(C$_1$-C$_6$)alkyl, hydroxy(C$_1$-C$_6$)alkoxy, oxo, amino(C$_1$-C$_6$)alkyl, (C$_1$-

$C_6$)alkylamino($C_1$-$C_6$)alkyl, di($C_1$-$C_6$)alkylamino($C_1$-$C_6$)alkyl amino($C_2$-$C_6$)alkoxy, ($C_1$-$C_6$)alkylamino($C_2$-$C_6$)alkoxy, di($C_1$-$C_6$)alkylamino($C_2$-$C_6$)alkoxy, ($C_1$-$C_6$)alkylcarbonyl, hydroxy($C_1$-$C_6$)alkylcarbonyl, ($C_1$-$C_6$)alkylhydroxycarbonyl, ($C_1$-$C_6$)alkylhydroxy($C_1$-$C_6$)alkyl, ($C_3$-$C_6$)cycloalkylcarbonyl, ($C_3$-$C_6$)cycloalkylaminocarbonyl, {($C_3$-$C_6$)cycloalkyl}{($C_1$-$C_6$)alkyl}aminocarbonyl, di($C_3$-$C_6$)cycloalkylaminocarbonyl, ($C_3$-$C_6$)cycloalkylaminosulfonyl, {($C_3$-$C_6$)cycloalkyl}{($C_1$-$C_6$)alkyl}aminosulfonyl, di($C_3$-$C_6$)cycloalkylaminosulfonyl, cyano($C_1$-$C_6$)alkyl, aminocarbonyl($C_1$-$C_6$)alkyl, ($C_1$-$C_6$)alkylaminocarbonyl($C_1$-$C_6$)alkyl, di($C_1$-$C_6$)alkylaminocarbonyl($C_1$-$C_6$)alkyl, ($C_3$-$C_6$)cycloalkylaminocarbonyl($C_1$-$C_6$)alkyl, {($C_3$-$C_6$)cycloalkyl}{($C_1$-$C_6$)alkyl}aminocarbonyl($C_1$-$C_6$)alkyl, [($C_1$-$C_6$)alkyl($C_4$-$C_6$)heterocyclyl]($C_1$-$C_6$)alkyl, and di($C_3$-$C_6$)cycloalkylaminocarbonyl($C_1$-$C_6$)alkyl;

$R^7$ and $R^8$ are independently hydrogen or alkyl; and $R^9$ is H or alkyl.

2. The compound of claim 1, wherein p is 0 or 1.

3. The compound of claim 1, wherein $R^1$ is halo.

4. The compound of claim 1, wherein $R^1$ is chloro.

5. The compound of claim 1, wherein $R^3$, $R^4$, and $R^5$ are each independently ($C_1$-$C_3$)alkyl or ($C_1$-$C_3$)alkoxy, cyano, carboxy, C(O)NH$_2$, N-methylamido, or acetylamino.

6. The compound of claim 1, wherein $R^3$ and $R^5$ are each ($C_1$-$C_3$)alkyl; and $R^4$ is ($C_1$-$C_3$)alkoxy.

7. The compound of claim 1, wherein $R^3$ and $R^5$ are each methyl; and $R^4$ is methoxy.

8. The compound of claim 1, wherein $R^2$ is monocyclic or bicyclic heteroaryl or mono- or bicyclic heterocyclyl, each of which are optionally substituted with 1 to 2 groups independently selected from $R^6$.

9. The compound according to claim 1 wherein $R^2$ is a 5 or 6-membered heterocyclyl containing 1 or 2 heteroatoms or a 5- or 6-membered heteroaryl containing 1 or 2 heteroatoms, the heteroatoms being either N or O.

10. The compound of claim 1, wherein $R^2$ is pyridyl, pyrazinyl, tetrahydronaphthalenyl, tetrahydroquinolinyl, 2,3-dihydrobenzo[b][1,4]dioxinyl, chromanyl, furyl, dihydrofuryl, tetrahydrofuryl, pyran, dihydropyran or oxane each of which are optionally substituted with 1 to 2 groups independently selected from $R^6$.

11. The compound of claim 1, wherein $R^2$ is pyridyl, pyrazinyl-2-yl, chroman-2-yl, chroman-3-yl, chroman-6-yl, chroman-7-yl, 2,3-dihydrobenzo[b][1,4]dioxine-2-yl, 2,3-dihydrobenzo[b][1,4]dioxine-6-yl, 5,6,7,8-tetrahydroquinolin-7-yl, 1,2,3,4-tetrahydronaphthalen-6-yl, 1,2,3,4-tetrahydronaphthalen-2-yl, oxanyl, pyranyl, dihydropyranyl, furyl, dihydrofuryl or tetra hydrofuryl each of which are optionally substituted with 1 to 2 groups independently selected from $R^6$.

12. The compound of claim 1, wherein $R^6$ is selected from hydrogen, halo, ($C_1$-$C_3$)alkyl, halo($C_1$-$C_3$)alkyl, ($C_1$-$C_3$)alkoxy, and halo($C_1$-$C_3$)alkoxy.

13. The compound of claim 1, wherein $R^2$ is pyridyl or oxanyl, where $R^2$, optionally substituted with 1 to 2 groups selected from halo, ($C_1$-$C_3$)alkyl, halo($C_1$-$C_3$)alkyl, ($C_1$-$C_3$)alkoxy, and halo($C_1$-$C_3$)alkoxy.

14. The compound of claim 1, wherein $R^2$ is unsubstituted pyridyl or oxanyl.

15. The compound of claim 1, wherein the compound is of Formula (III):

(III)

or a pharmaceutically acceptable salt thereof, wherein $R^1$ is halo;

$R^3$ and $R^5$ are ($C_1$-$C_3$)alkyl;

$R^4$ is ($C_1$-$C_3$)alkoxy; and $R^6$ is selected from hydrogen, halo, ($C_1$-$C_3$)alkyl, halo($C_1$-$C_3$)alkyl, ($C_1$-$C_3$)alkoxy, and halo($C_1$-$C_3$)alkoxy.

16. The compound of claim 15, wherein $R^6$ is hydrogen.

17. The compound of claim 1, wherein the compound is of Formula IV or pharmaceutically acceptable salt thereof, wherein $R^1$, $R^3$, $R^4$ and $R^5$ are each independently halo, ($C_1$-$C_3$) alkyl, halo ($C_1$-$C_3$alkyl), ($C_1$-$C_3$) alkoxy, or halo ($C_1$-$C_3$) alkoxy, and $R^6$ is hydrogen, alkyl, aryl or 5- or 6-membered heteroaryl containing nitrogen as the only ring heteroatom, wherein the aryl and heteroaryl group is unsubstituted or substituted with halo, alkyl, or haloalkyl.

18. The compound of claim 17 wherein p is 0.

19. The compound of claim 17, wherein $R^1$ is halo;

$R^3$ and $R^5$ are independently $C_1$-$C_3$ alkyl $R^4$ is $C_1$-$C_3$ alkoxy and $R^6$ is pyridyl or phenyl, which $R^2$ may be unsubstituted or substituted with alkyl or halo or $R^6$ is hydrogen or alkyl.

20. The compound of claim 17, wherein $R^6$ is hydrogen, 4-fluorophenyl, 2-pyridyl or 5-methyl-2-pyridyl.

21. A compound of the formula:

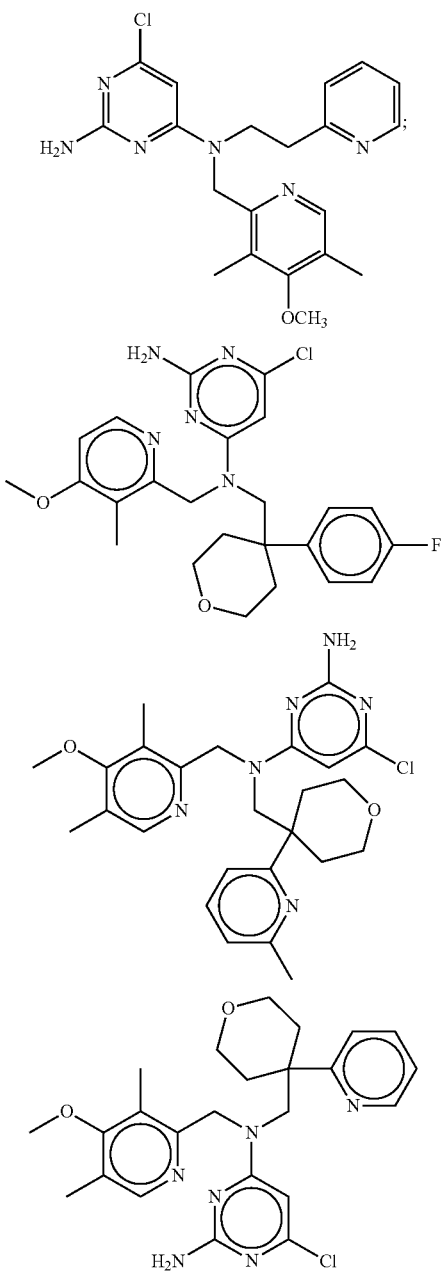

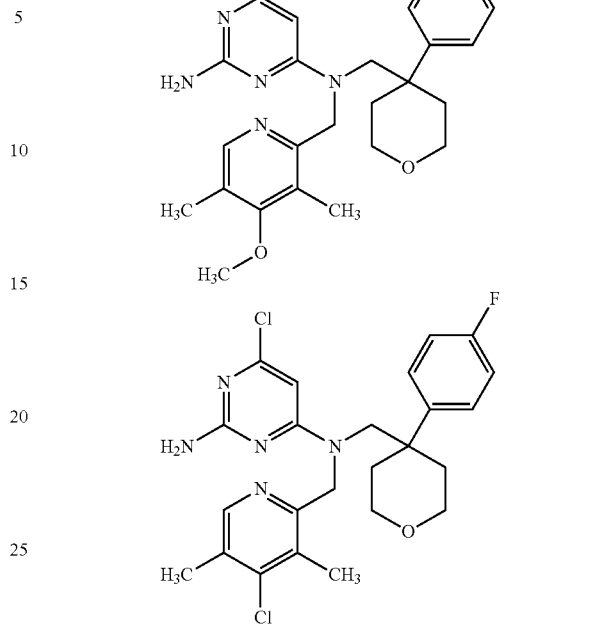

or a pharmaceutically acceptable salt thereof.

22. A pharmaceutical composition comprising a compound according to claim 1, or a pharmaceutically acceptable salt thereof and a pharmaceutically acceptable carrier.

23. A method of treating Glioblastoma multiforme (GBM) in a subject, the method comprising administering to the subject a therapeutically effective amount of a compound according to claim 1, or a pharmaceutically acceptable salt thereof.

24. A pharmaceutical composition comprising a compound according to claim 17, or a pharmaceutically acceptable salt thereof; and a pharmaceutically acceptable carrier.

25. A pharmaceutical composition comprising a compound according to claim 21, or a pharmaceutically acceptable salt thereof; and a pharmaceutically acceptable carrier.

26. A method of treating Glioblastoma multiforme (GBM) in a subject, the method comprising administering to the subject a therapeutically effective amount of a compound according to claim 17, or a pharmaceutically acceptable salt thereof.

27. A method of treating Glioblastoma multiforme (GBM) in a subject, the method comprising administering to the subject a therapeutically effective amount of a compound according to claim 21, or a pharmaceutically acceptable salt thereof.

* * * * *